United States Patent
Gilbert

(10) Patent No.: US 6,632,824 B2
(45) Date of Patent: Oct. 14, 2003

(54) ARYL-8-AZABICYCLO[3.2.1]OCTANES FOR THE TREATMENT OF DEPRESSION

(75) Inventor: Adam M. Gilbert, Congers, NY (US)

(73) Assignee: Wyeth, Madison, NJ (US)

( * ) Notice: Subject to any disclaimer, the term of this patent is extended or adjusted under 35 U.S.C. 154(b) by 0 days.

(21) Appl. No.: 10/151,210

(22) Filed: May 20, 2002

(65) Prior Publication Data

US 2003/0032645 A1 Feb. 13, 2003

Related U.S. Application Data

(60) Provisional application No. 60/293,563, filed on May 25, 2001.

(51) Int. Cl.[7] .................. A61K 31/46; C07D 451/02
(52) U.S. Cl. .................. 514/304; 546/126; 546/124; 546/112; 514/299
(58) Field of Search ................. 514/304, 299; 546/126, 124, 112

(56) References Cited

U.S. PATENT DOCUMENTS

| | | |
|---|---|---|
| 5,340,936 A | 8/1994 | Glamkowski et al. |
| 5,614,523 A | 3/1997 | Audia et al. |
| 5,627,196 A | 5/1997 | Audia et al. |
| 5,741,789 A | 4/1998 | Hibschman et al. |
| 5,789,402 A | 8/1998 | Audia et al. |

FOREIGN PATENT DOCUMENTS

| | | | |
|---|---|---|---|
| WO | WO 97/13770 | 4/1997 | |
| WO | WO 97/16451 | 5/1997 | |
| WO | WO 97/48698 A1 | 12/1997 | |
| WO | WO 99/65492 | 12/1999 | |
| WO | WO 00/04017 A1 | 1/2000 | |
| WO | 01/32179 | * 5/2001 | .......... 514/304 |
| WO | 01/46187 | * 6/2001 | .......... 514/304 |

OTHER PUBLICATIONS

Perregaard, et al., J. Med. Chem., 38(11), 1998–2008 (1995).
TiPS, Jul. 1993, vol. 14, p. 262, 5–HT and Antidepressants: New Views from Microdialysis Studies, F. Artigas.
Psycholopharmacology, 1991, 105: 415–420, Long–term Fluoxetine Treatment Decreases 5–HT 1A Receptor Responsivity in Obsessive–Compulsive Disorder, Lesch et al.
Arch Gen Psychiatry, Mar. 1994, vol. 51, p. 248–251, Pindolol Induces a Rapid Improvement of Depressed Patients Treated with Serotonin Reuptake Inhibitors, F. Artigas et al.
Arch Gen Psychiatry, Apr. 1999, vol. 56, p. 375–379, A Double–blind, Randomized, Placebo–Controlled Trial of Pindolol Augmentation in Depressive Patients Resistant to Serotonin Reuptake Inhibitors, Perez, et al.
Richard E. Mewshaw et al., J. Med. Chem., 40, 4235–4256 (1997).

* cited by examiner

*Primary Examiner*—Charanjit S. Aulakh
(74) *Attorney, Agent, or Firm*—Joseph M. Mazzarese; Kimberly R. Hild

(57) ABSTRACT

The present invention includes compounds of formula I

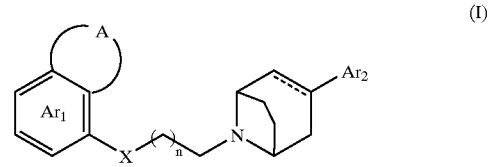

(I)

wherein A, X, n, $Ar_1$, and $Ar_2$ are defined as set forth herein. These compounds may be used to treat depression. The invention also includes formulations containing these compounds, and methods for making and using compounds of this invention.

22 Claims, No Drawings

ARYL-8-AZABICYCLO[3.2.1]OCTANES FOR THE TREATMENT OF DEPRESSION

BACKGROUND OF INVENTION

The present invention relates to aryl-8-azabicyclo[3.2.1] octane and aryl-8-azabicyclo[3.2.1]oct-2-ene derivatives having pharmacological activity, and to their use in the treatment of diseases affected by disorders of the serotonin affected neurological systems, such as depression and anxiety.

Pharmaceuticals which enhance serotonergic neurotransmission are useful for the treatment of many psychiatric disorders, including depression and anxiety. The first generation of non-selective serotonin-affection drugs operated through a variety of physiological functions which endowed them with several side effect liabilities. The more currently prescribed drugs, the selective serotonin reuptake inhibitors (SSRIs), act predominately by inhibiting 5-HT, which is released at the synapses, from being actively removed from the synaptic cleft via a presynaptic serotonin transport carrier (5-HT-T).

The present invention relates to a new class of molecules which have the ability to act at the 5-HT transporter. Such compounds are therefore potentially useful for the treatment of depression as well as other serotonin disorders.

Some of the present molecules have a second activity as partial agonists/inhibitors of the serotonin $1_A$ receptor (5-HT$_{1A}$). Since SSRIs require several weeks before a full therapeutic effect is seen, their mechanism of action can't solely be explained by the inhibition of 5-HT-T. It is believed that this delayed effect is due to the involvement of 5-HT$_{1A}$ autoreceptors. It has been previously suggested (Artigas et al. *TiPs*, 1993, 14, 262) that the efficacy of reuptake inhibitors may be attenuated by the activation of 5-HT$_{1A}$ receptors which results in the reduced firing rate of 5-HT neurons. Repeated SSRI administration, causing desensitization of 5-HT$_{1A}$ receptors, is postulated to be required before the antidepressant effect of these compounds is seen. Support for desensitization of 5-HT$_{1A}$ in humans is shown by an obsessive-compulsive disorder (OCD) study (Lesch et al. *Psychopharm.* 1991, 105, 415), where patients given repeated treatment with SSRIs developed tolerance to the hypothermic response induced by the administration of the 5-HT$_{1A}$ antagonist ipsapirone. Thus a dual SSRI/5-HT$_{1A}$ antagonists should provide antidepressant activity with a rapid onset of action. Studies using a combination of an SSRI (fluoxetine) and a 5-HT$_{1A}$ antagonists (pindolol) appear to support this hypothesis (Artigas et. al. *Arch. Gen. Psychiat.* 1994, 51, 248 and Perez et al. *Arch. Gen. Psychiat* 1999, 56, 375).

Aryloxyalkyl amines have previously been shown to effect 5-HT-reuptake. U.S. Pat. No. 5,614,523 (Audia et al.) discloses a series of indoloxyethylpiperazines which affect the 5-HT$_{1A}$ and 5-HT-T receptors. U.S. Pat. No. 5,627,196 (Audia et al.) discloses a series of indoloxyethyltetrahydropyridines and indolyoxyethylpiperidinols which affect the 5-HT$_{1A}$ and 5-HT-T receptors. U.S. Pat. No. 5,741,789 (Hibschman et al.) teaches a series of quinolinoxyethylpiperidines which affect the 5-HT$_{1A}$ and 5-HT-T receptors. U.S. Pat. No. 5,789,402 (Audia et al.) discloses a series of indoloxyethylpiperidines which affect the 5-HT$_{1A}$ and 5-HT-T receptors. The current invention differs from the these patents in that the 8-azabicyclo[3.2.1]octane and 8-azabicyclo[3.2.1]oct-2-ene ring structures are used instead of the corresponding piperidines/tetrahydropyridines.

8-Azabicyclo[3.2.1]octanes and 8-azabicyclo[3.2.1]oct-2-enes have previously been shown to effect 5-HT-T reuptake. WO 9713770 (Moldt et al.) teaches a series of phenyl tropenes which affect the 5-HT-T receptor. WO 9716451 (Scheel-Krügger et al.) discloses a series of fused tropane derivatives which act as neurotransmitter reuptake inhibitors. WO 9965492 (Audia et al.) provides a series of aryl tropenes/tropanes that affect the 5-HT-T receptor in. The current invention differs from these references in that an aryloxy alkyl chain has been attached to the aryl 8-azabicyclo[3.2.1]octane and aryl 8-azabicyclo[3.2.1]oct-2-ene structures.

SUMMARY OF THE INVENTION

The present invention comprises compounds represented by the formula I:

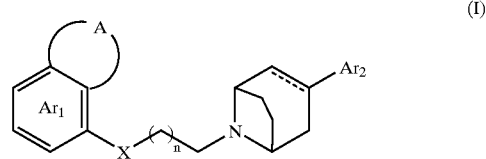

(I)

wherein:
A is an optional residue which combines with the carbon atoms to which it is attached to complete a cyclobutyl, cyclopentyl, cyclohexyl, cycloheptyl, dioxinyl, pyrrolyl, imidazolyl, pyridinyl, pyridazynyl or pyrimidinyl group;

X is NH, O or S;

n is an integer from 0 to 3;

Ar$_1$ is phenyl or pyridyl substituted with 0–2 substituents selected from the group consisting of C$_1$–C$_3$ alkyl, C$_1$–C$_3$ alkoxy, halo, cyano, nitro, trifluoromethyl, difluoromethyl, hydroxyl, and trifluoromethoxy groups and combinations thereof;

Ar$_2$ is indolyl, benzimidazolyl, phenyl, naphthyl, anthracenyl, phenanthrenyl, benzyl, benzofuryl, or benzothienyl, substituted with 0–2 C$_1$–C$_3$ alkyl, C$_1$–C$_3$ alkoxy, halo, cyano, nitro, trifluoromethyl, difluoromethyl, hydroxyl, or trifluoromethoxy groups;

and all crystalline forms and pharmaceutically acceptable salts thereof.

The present invention further comprises a pharmaceutical composition which comprises a compound of this invention in combination or association with a pharmaceutically acceptable carrier.

The present invention also comprises methods of making and using the compounds and formulations of this invention, which methods are described in further detail below.

DETAILED DESCRIPTION

A preferred aspect of this invention comprises compounds of formula I wherein:

A is a residue which combines with the carbon atoms to which it is attached to complete a cyclopentyl, cyclohexyl, pyrrolyl, or pyridinyl, group X is an NH, O or S moiety n is 1–2;

Ar$_1$ is a phenyl group substituted with 0–2 substituents selected from C$_1$–C$_3$ alkyl, C$_1$–C$_3$ alkoxy, halo, cyano, trifluoromethyl, hydroxyl, and trifluoromethoxy groups and combinations thereof;

Ar₂ is indolyl, phenyl, naphthyl, benzofuryl, or benzothienyl, substituted with 0–2 $C_1$–$C_3$ alkoxy, halo, cyano, nitro, trifluoromethyl, difluoromethyl, hydroxyl, or trifluoromethoxy groups;

and all crystalline forms and pharmaceutically acceptable salts thereof.

More preferred compounds of this invention are compounds of formula I wherein:

A is a residue which combines with the carbon atoms to which it is attached to complete a pyrrolyl, or pyridinyl, group X is an NH, or O moiety n is 1;

Ar₁ is phenyl substituted with 0–2 groups selected from $C_1$–$C_3$ alkoxy, halo, trifluoromethyl, trifluoromethoxy, and combinations thereof;

Ar₂ is indolyl, naphthyl, benzofuryl, or benzothienyl, substituted with 0–2 halo, cyano, trifluoromethyl, difluoromethyl, hydroxyl, or trifluoromethoxy groups;

and all crystalline forms and pharmaceutically acceptable salts thereof.

In this specification, the term alkyl, whether used alone or as part of another group, includes straight and branched chain alkyl groups containing from 1 to 3 carbon atoms. For example, methyl, ethyl, propyl, isopropyl, are encompassed by the term alkyl. The alkyl group may be substituted or unsubstituted. The aforementioned number of carbon atoms in the alkyl group refers to carbon backbone and does not include carbon atoms of substituents, such as alkoxy substitutions and the like.

Alkoxy, whether used alone or as part of another group include straight and branched chain alkoxy groups containing from 1 to 3 carbon atoms. For example, methoxy, ethoxy, propoxy, isopropoxy, are encompassed by the term alkoxy. The alkoxy group may be substituted or unsubstituted. The aforementioned number of carbon atoms in the alkoxy group does not include carbon atoms of substituents, such as alkyl substitutions and the like.

Halogen or halo as used herein means chlorine, bromine, iodine and fluorine.

Highly preferred compounds of the present invention include:

4-[2-(3-Naphthalen-2-yl-8-aza-bicyclo[3.2.1]oct-2-en-8-yl)-ethoxy]-1H-indole or a pharmaceutically acceptable salt thereof;

3-{8-[2-(1H-Indol-4-yloxy)ethyl]-8-azabicyclo[3.2.1]oct-2-en-3-yl}-1H-indole or a pharmaceutically acceptable salt thereof;

2-[3-(1H-indol-3-yl)-8-azabicyclo[3.2.1]oct-2-en-8-yl]ethyl 5-quinolinyl ether or a pharmaceutically acceptable salt thereof;

8-[2-(2,3-Dihydro-benzo[1,4]dioxin-5-yloxy)-ethyl]-3-naphthalen-2-yl-8-aza-bicyclo[3.2.1]oct-2-ene or a pharmaceutically acceptable salt thereof;

6-methoxy-N-{2-[3-(2-naphthyl)-8-azabicyclo[3.2.1]oct-2-en-8-yl]ethyl}-8-quinolinamine or a pharmaceutically acceptable salt thereof;

6-Chloro-N-{2-[3-(2-naphthyl)-8-azabicyclo[3.2.1]oct-2-en-8-yl]ethyl}-8-quinolinamine or a pharmaceutically acceptable salt thereof;

N-{2-[3-(2-naphthyl)-8-azabicyclo[3.2.1]oct-2-en-8-yl]ethyl}-8-quinolinamine or a pharmaceutically acceptable salt thereof;

6-Methoxy-8-[2-(3-naphthalen-2-yl-8-azabicyclo[3.2.1]oct-2-en-8-yl)-ethoxy]-quinoline or a pharmaceutically acceptable salt thereof;

8-[2-(Indan-4-yloxy)-ethyl]-3-naphthalen-2-yl-8-azabicyclo[3.2.1]oct-2-ene or a pharmaceutically acceptable salt thereof;

4-{2-[3-(6-Methoxy-naphthalen-2-yl)-8-aza-bicyclo[3.2.1]oct-2-en-8-yl]-ethoxy}-1H-indole or a pharmaceutically acceptable salt thereof;

3-Naphthalen-2-yl-8-[2-(3-trifluoromethyl-phenoxy)-ethyl]-8-aza-bicyclo[3.2.1]oct-2-ene or a pharmaceutically acceptable salt thereof;

4-[2-(3-Naphthalen-2-yl-8-aza-bicyclo[3.2.1]oct-8-yl)-ethoxy]-1H-indole or a pharmaceutically acceptable salt thereof;

4-{2-[3-(3,4-Dichloro-phenyl)-8-aza-bicyclo[3.2.1]oct-2-en-8-yl]-ethoxy}-1H-indole or a pharmaceutically acceptable salt thereof;

3-{8-[3-(1H-indol-4-yloxy)propyl]-8-azabicyclo[3.2.1]oct-2-en-3-yl}-1H-indole or a pharmaceutically acceptable salt thereof;

4-[3-(3-Naphthalen-2-yl-8-aza-bicyclo[3.2.1]oct-2-en-8-yl)-propoxy]-1H-indole or a pharmaceutically acceptable salt thereof;

4-{3-[3-(3,4-Dichlorophenyl)-8-azabicyclo[3.2.1]oct-2-en-8-yl]propoxy-1H-indole or a pharmaceutically acceptable salt thereof;

8-{2-[3-(2-Naphthyl)-8-azabicyclo[3.2.1]oct-8-yl]ethoxy}quinoline or a pharmaceutically acceptable salt thereof; and, 8-({2-[3-(2-naphthyl)-8-azabicyclo[3.2.1]oct-8-yl]ethyl}sulfanyl) quinoline or a pharmaceutically acceptable salt thereof.

It is understood that the definition of the compounds of formula I, when Ar contains asymmetric carbons, encompasses all possible stereoisomers and mixtures thereof which possess the activity discussed below. In particular, it encompasses racemic modifications and any optical isomers which possess the indicated activity. Optical isomers may be obtained in pure form by standard separation techniques known in the art.

Pharmaceutically acceptable salts are those derived from organic and inorganic acids such as: lactic, citric, acetic, tartaric, succinic, maleic, malonic, oxalic, fumaric, hydrochloric, hydrobromic, phosphoric, nitric, sulfuric, methanesulfonic, and the like. Where Ar contain a carboxyl group, salts of the compounds of this invention may be formed with bases such as alkali metals (Na, K, Li) or the alkaline earth metals (Ca or Mg), and the like.

The compounds of formula I have been found to have affinity for the 5-HT reuptake transporter. They are therefore useful in the treatment of diseases affected by disorders of the serotonin affected neurological systems, such as depression and anxiety.

The present invention further provides a pharmaceutical composition which comprises a compound of this invention in combination or association with a pharmaceutically acceptable carrier. The compositions are preferably adapted for oral or subcutaneous administration. However, they may be adapted for other modes of administration.

The compounds of this invention may be administered orally or parenterally, neat or in combination with conventional pharmaceutical carriers. Applicable solid carriers can include one or more substances which may also act as flavoring agents, lubricants, solubilizers, suspending agents, fillers, glidants, compression aids, binders or tablet-disintegrating agents or an encapsulating material. In powders, the carrier is a finely divided solid which is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Any of the solid carriers known to those skilled in the art may be used with the compounds of this invention. Particularly suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidone, low melting waxes and ion exchange resins.

Liquid carriers may be used in preparing solutions, suspensions, emulsions, syrups and elixirs of the compounds of this invention. The compounds of this invention can be dissolved or suspended in a pharmaceutically acceptable liquid carrier such as water, an organic solvent, a mixture of both or pharmaceutically acceptable oils or fat. Suitable examples of liquid carriers for oral and parenteral administration include water, alcohols (including monohydric alcohols and polyhydric alcohols, e.g., glycols) and their derivatives and oils (e.g., fractionated coconut oil and arachis oil). For parenteral administration, the carrier can also be an oily ester such as ethyl oleate and isopropyl myristate. Sterile liquid carriers are used in compositions for parenteral administration.

Liquid pharmaceutical compositions which are sterile solutions or suspensions can be utilized by, for example, intramuscular, intraperitoneal or subcutaneous injection. Sterile solutions can also be administered intravenously. Compositions for oral administration may be either liquid or solid composition form.

In order to obtain consistency of administration, it is preferred that a composition of the invention is in the form of a unit dose. Suitable unit dose forms include tablets, capsules and powders in sachets or vials. Such unit dose forms may contain from 0.1 to 100 mg of a compound of the invention and preferably from 2 to 50 mg. Still further preferred unit dosage forms contain 5 to 25 mg of a compound of the present invention. The compounds of the present invention can be administered orally at a dose range of about 0.01 to 100 mg/kg or preferably at a dose range of 0.1 to 10 mg/kg. Such compositions typically may be administered from 1 to 6 times a day, more usually from 1 to 4 times a day.

The compositions of the invention may be formulated with conventional excipients, such as a filler, a disintegrating agent, a binder, a lubricant, a flavoring agent, and the like. They are formulated in a conventional manner, for example, in a manner similar to those used for known antihypertensive agents, diuretics and β-blocking agents.

The compounds of formula I may be synthesized as described below:

In one aspect of the present invention, compounds of formula I where X=NH, O or S and A=pyrrole may be prepared by reacting the corresponding Ar$_2$-8-azabicyclo[3.2.1]-octane or -octene compound with the corresponding pyrrolyl-Ar$_1$—X—(CH$_2$)$_n$—CH$_2$-halide in the presence of an appropriate solvent and base, as exemplified in Scheme I. Thus a compound of formula III is reacted with a compound of formula IV in the presence of an appropriate solvent such as DMSO, DMF, EtOH, or MeOH and in the presence of a base such as K$_2$CO$_3$, Et$_3$N, or i-Pr$_2$NEt at 80° C. to give a compound of formula II.

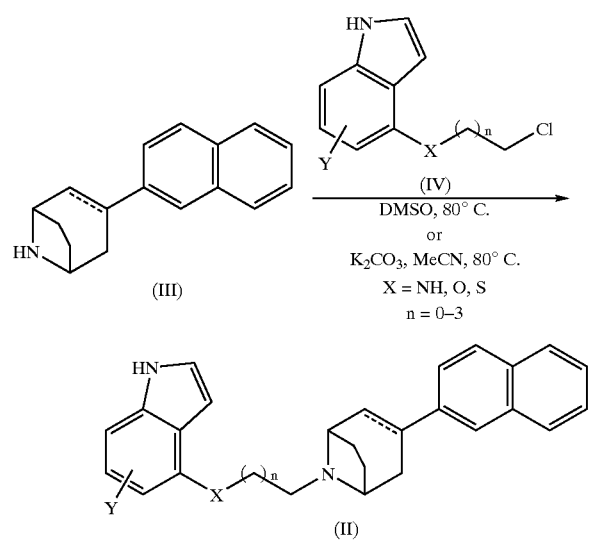

Naphthyl-8-azabicyclo[3.2.1]octenes/naphthyl-8-azabicyclo[3.2.1]octanes of formula III may prepared according to Scheme II. Thus bromonapthalene (formula V) and other bromoarenes may be lithiated by reaction with n-BuLi, s-BuLi or t-BuLi in an etherial solvent such THF, DME or Et$_2$O, followed by addition of N-Boc-tropinone to give tropinol (formula VI). Treatment of tropinol with TFA or other acids in a solvent such as CH$_2$Cl$_2$, CHCl$_3$ or Cl(CH$_2$)$_2$Cl causes deprotection of the Boc group as well as elimination of H$_2$O to give naphthyl-8-azabicyclo[3.2.1]octene (formula VII). In addition to Boc, other nitrogen protecting groups useful for these reactions are well known by the skilled artisan (for example, see Greene and Wuts, *Protective Groups in Organic Synthesis*, 3$^{rd}$ Edition, Wiley Interscience, New York, 1999) and may be used in the practice of this invention. Reduction of naphthyl-8-azabicyclo[3.2.1]octene (formula VII) to the corresponding saturated naphthyl-8-azabicyclo[3.2.1]octane (formula VIIa) can be accomplished via hydrogenation conditions using a precious metal catalyst such as palladium on carbon in an appropriate solvent such as EtOH, EtOAc or MeOH.

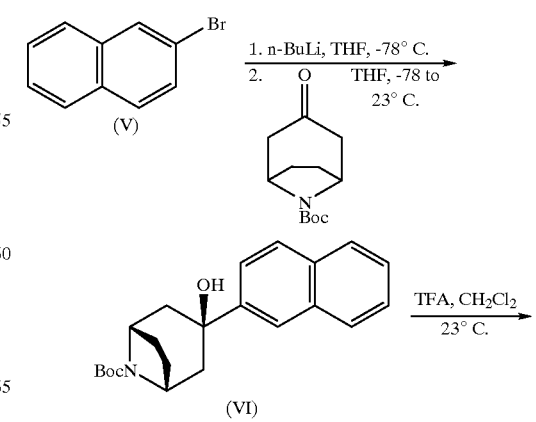

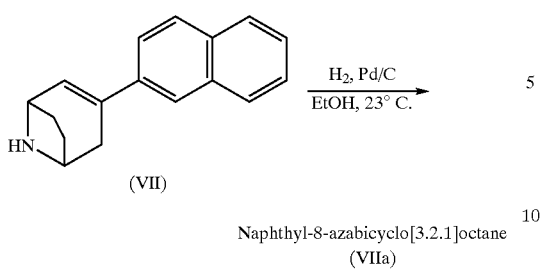

Naphthyl-8-azabicyclo[3.2.1]octane (VIIa)

Compounds of formula IV may be prepared according to Scheme III. Thus, thio, amino and oxyindoles are reacted with 2-chloromethanol, 2-chloroethanol, 2-chloro-n-propanol or 2-chloro-n-butanol in the presence of diethyl- or diisopropylazodicarboxylate, and triphenylphosphine, in a suitable solvent such as THF, $CH_2Cl_2$ or MeCN to produce IV according to the procedure of Mitsunobu in *Synthesis* 1981, 1; recent review: Hughs, *Org. React.* 1992, 42, 337. Similar thio, amino and oxy-heterocyclic compounds may be prepared similarly.

Scheme III

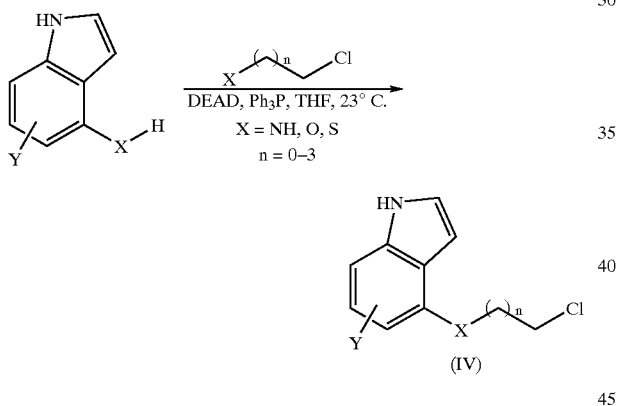

Compounds of formula I where X=NH, O or S, $Ar_1$ is phenyl and A=pyridinyl (NH, O and S substituents are in the 8-position of the quinoline) require a different preparation route due to the position of the quinoline nitrogen. Compounds of formula I, where X=NH, $Ar_1$ is phenyl and A=pyridinyl may be prepared by reacting the corresponding 8-haloquinoline with the corresponding $Ar_2$-8-azabicyclo [3.2.1]oct(a/e)ne-$CH_2$—$(CH_2)_n$—$NH_2$ compound in the presence of NaOt-Bu and a suitable catalyst, as exemplified in Scheme IV. Thus, compounds of formula IX are reacted with compounds of formula X, catalytic $Pd_2dba_3$ or $Pd(OAc)_2$, catalytic BI NAP or other suitable phosphine ligands known to a skilled artisan, in the presence of NaOt-Bu, in PhMe or THF at 80° C. to give compounds of type VII in accordance with the procedure descirbed by Buchwald in *Angew. Chem., Int. Ed. Engl.* 1995, 34, 1348.

Scheme IV

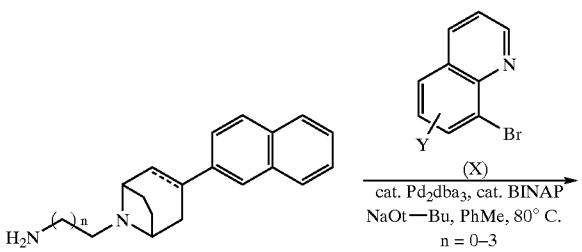

Compounds of formula IX may be prepared according to Scheme V. Alkylation of the secondary amine in a compound of formula VII or formula VIIa with 2-(N-Boc amino)ethyl chloride (prepared according to the procedure of Tanaka (*Chem. Pharm. Bull.* 1988, 36, 3125) in the presence of $Et_3N$ in a solvent such as $CH_2Cl_2$ or DMF gives the N-Boc ethylamine derivative of formula XI. Removal of the Boc group is accomplished by treatment with TFA in a solvent such as $CH_2Cl_2$ to give naphthyl-8-azabicyclo[3.2.1] octene/naphthyl-8-azabicyclo[3.2.1]octane of formula IX.

Scheme V

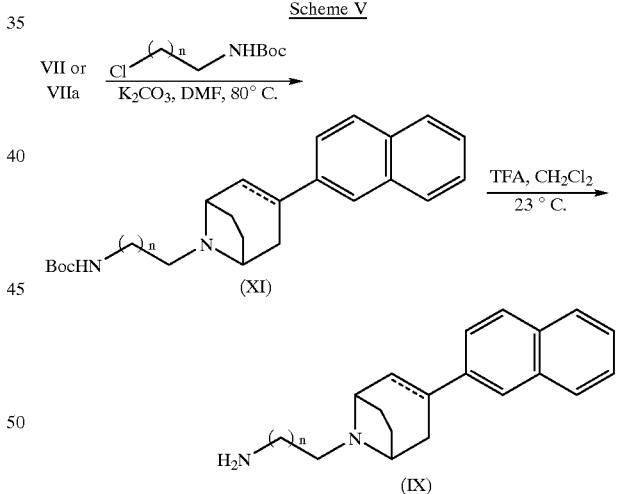

In the case where the bromoarene is a 3-bromoindole, 3-indolyltropene (formula IX) may be synthesized according to Scheme VI. Thus 3-Br-N-TBS-indole (formula XII), prepared according to the procedure of Bosch in *J. Org. Chem.* 1994, 59, 10, is lithiated using an alkyl lithium such as t-BuLi and then reacted with N-Boc-tropinone to give tropinol (formula XIII). Deprotection of both the TBS groups and elimination of $H_2O$ occurs with TFA or other acids to give 3-indole-8-azabicyclo[3.2.1]octene XIV. Reduction using hydrogen gas, a precious metal catalyst such as palladium on carbon in a suitable solvent such as EtOH, MeOH, or EtOAc gives indole-8-azabicyclo[3.2.1] octane XIVa.

Scheme VI

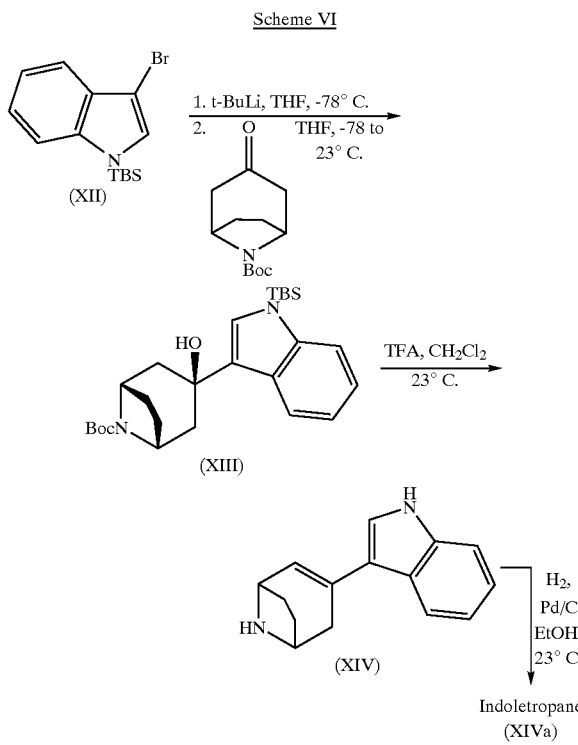

8-Bromoquinolines, such as a compound according to formula X, may be synthesized as shown in Scheme VII. 2-Nitroanilines of formula XV may be converted to their corresponding nitroquinolines (formula XVI) via a Skraup reaction using glycerol, 3-$NO_2PhSO_3Na$ in hot concentrated $H_2SO_4$ according to Palmer in *J. Chem. Soc.* 1962, 3645, reduction of the nitroquinoline to the corresponding quinolineamine (formula XVII) may be accomplished using $H_2$, a precious metal catalyst such as Pd on carbon in a solvent such as EtOAc or EtOH or iron, $NH_4Cl$ and $H_2O$ in an alcoholic solvent. Diazotization of the compound of formula XVII using $NaNO_2$ in HBr, followed by heating in the presence of CuBr and additional HBr at an elevated temperature produces the 8-bromoquinoline of formula X.

Scheme VII

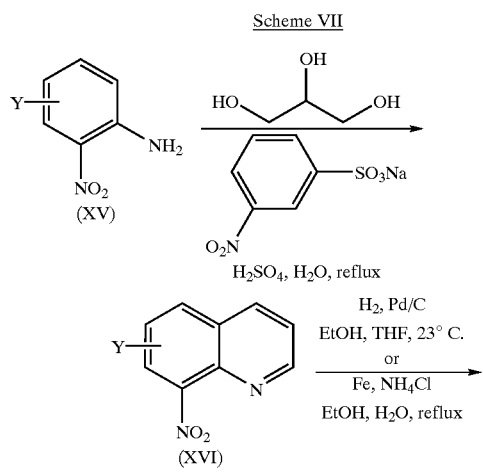

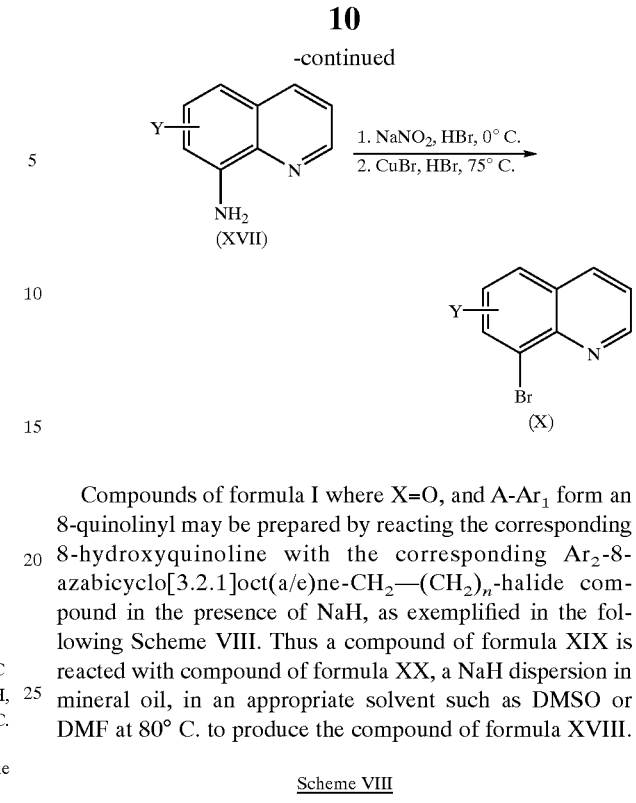

Compounds of formula I where X=O, and A-$Ar_1$ form an 8-quinolinyl may be prepared by reacting the corresponding 8-hydroxyquinoline with the corresponding $Ar_2$-8-azabicyclo[3.2.1]oct(a/e)ne-$CH_2$—$(CH_2)_n$-halide compound in the presence of NaH, as exemplified in the following Scheme VIII. Thus a compound of formula XIX is reacted with compound of formula XX, a NaH dispersion in mineral oil, in an appropriate solvent such as DMSO or DMF at 80° C. to produce the compound of formula XVIII.

Scheme VIII

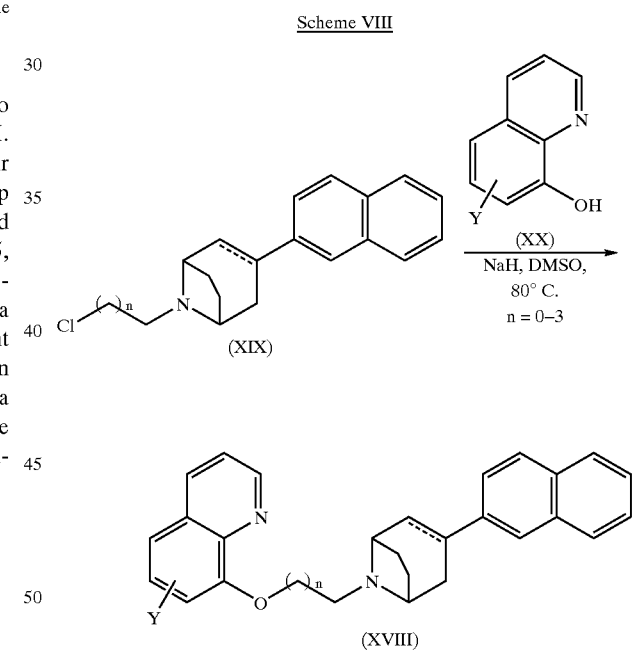

Naphthyl-8-azabicyclo[3.2.1]octene/naphthyl-8-azabicyclo[3.2.1]octane (formula XIX) may be prepared according to Scheme IX. Thus naphthyl-8-azabicyclo[3.2.1] octenes/naphthyl-8-azabicyclo[3.2.1]octanes of formulae VII and VIIa are reacted with 2-bromoethanol in the presence of $K_2CO_3$ at 80° C. in an appropriate solvent such as DMF, DMSO or EtOH to produce the compound of formula XXII. Conversion to the corresponding chloride (formula XIX) may be accomplished using MsCl, a tertiary amine base such as $Et_3N$ or i-$Pr_2NEt$ in a solvent such as $CH_2Cl_2$, $Cl(CH_2)_2Cl$ or DMF.

Scheme IX

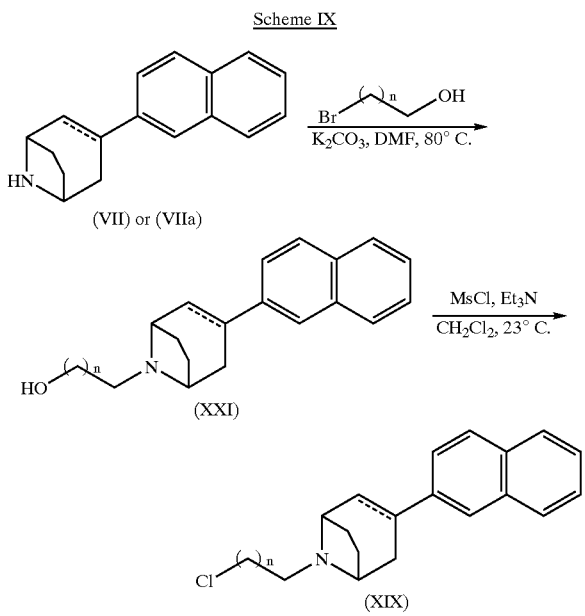

The sequence in Scheme VI may also be applied to indoles of formulae XIV and XIVa to synthesize the corresponding indoles of formula XIX or formula XVII.

Compounds of formula I where X=S may be prepared by reacting the corresponding 8-thioquinoline with the corresponding $Ar_2$-8-azabicyclo[3.2.1]oct(a/e)ne-$CH_2$—$(CH_2)_n$-halide compound in the presence of NaH, as exemplified in the following Scheme X. Thus a compound of formula XIX may be reacted with a compound of formula XXIII in a suitable solvent such as DMSO, DMF, MeCN or EtOH at an elevated temperature such as 50° C. to produce a compound of formula XXII. The synthesis of compounds of formula XIX is illustrated in Scheme IX, above.

Scheme X

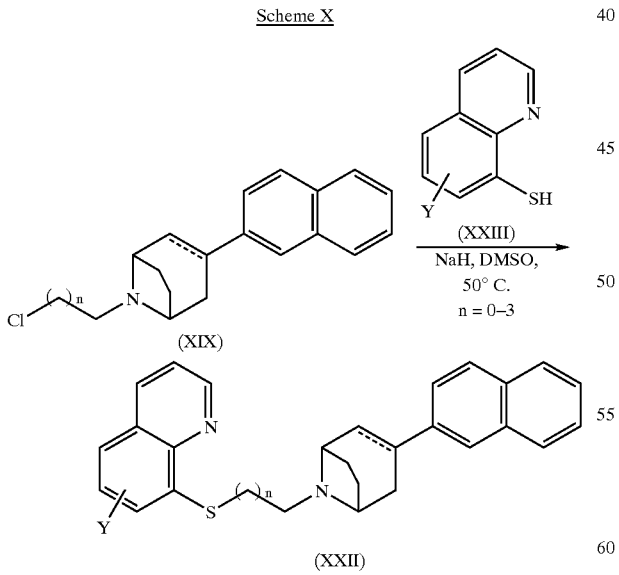

The synthesis of compounds of formula XXIII is shown in Scheme XI, in which a compound of formula X is reacted with an alkyllithium such as n-BuLi, s-BuLi or t-BuLi in an etherial solvent such THF or $Et_2O$, allowed to stir for 0 to 60 minutes and then quenched with a slurry of $S_8$ in benzene or toluene according to the procedure of Bergman et al. *Isr. J. Chem.* 1969, 7, 477.

Scheme XI

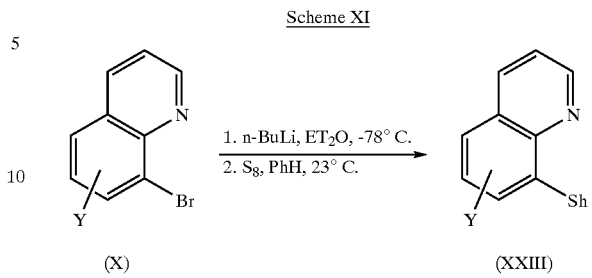

The present invention further provides a compound of the invention for use as an active therapeutic substance. Compounds of formula I are of particular use in the treatment of diseases affected by disorders of the serotonin.

The present invention further provides a method of treating depression and anxiety in mammals including man, which comprises administering to the afflicted mammal an effective amount of a compound or a pharmaceutical composition of the invention.

The following examples are presented to illustrate certain embodiments of the present invention, but should not be construed as limiting the scope of this invention.

EXAMPLE 1

4-[2-(3-Naphthalen-2-yl-8-aza-bicyclo[3.2.1]oct-2-en-8-yl)-ethoxy]-1H-indole

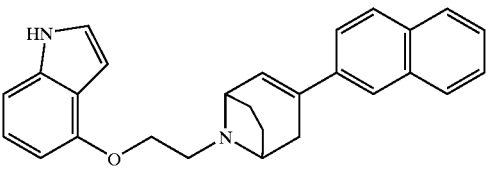

Step 1

4-(2-Chloro-ethoxy)-1H-indole

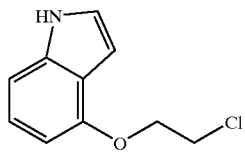

To 2.0 g (1.5 mmol) 4-hydroxyindole in 50 mL THF at 0° C. is added 6.3 g (24 mmol) $Ph_3P$, 1.51 mL (1.81 g, 22.53 mmol) 2-chloroethanol and 3.78 mL (4.19 g, 24.03 mmol) diethylazodicarboxylate. After stirring at 23° C. for 20 h, the dark reaction mixture is evaporated to a black oil. Diethyl ether (30 mL) is added, the dark solution stirred on a magnetic stir plate, and 200 mL hexanes is added (to precipitate $Ph_3PO$). After stirring at 23° C. for 30 min, the mixture is filtered and the filtrate evaporated to a light yellow oil. Flash chromatography on $SiO_2$ gel, eluting with hexanes/EtOAc (8/1 to 4/1), gives 1.13 g (5.78 mmol, a 39% yield) of the title compound as an off-white solid. MS (ES) m/z 196 $(MH)^+$.

Step 2

3-Hydroxy-3-naphthalen-2-yl-8-aza-bicyclo[3.2.1]
octane-8-carboxylic Acid Tert-Butyl Ester

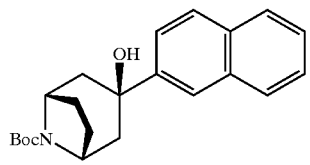

To a −78° C. solution of 6.20 g (29.9 mmol) 2-bromonaphthalene and 125 mL THF is added 12 mL of 2.5 M n-BuLi/hexanes. After stirring at −78° C. for 30 mins a solution of 6.40 g (28.4 mmol) 3-oxo-8-aza-bicyclo[3.2.1]octane-8-carboxylic acid tert-butyl ester and 14 mL THF is added dropwise. The reaction is allowed to proceed at −78° C. for 30 mins and then warmed to 23° C. over 6 h. After quenching with 100 mL 1N NaOH and extraction with 3×100 mL of EtOAc, the combined organics are washed with 1×100 mL $H_2O$, 1×100 mL brine, dried over $MgSO_4$, filtered, and the volatiles removed. Flash chromatography in $SiO_2$ gel, eluting with hexanes/EtOAc (4/1 to 1/1) gives 7.00 g (19.8 mmol, a 66% yield) of the title compound as a white solid. MS (ES) m/z 354 ($M^++H$, 100).

Step 3

3-Naphthalen-2-yl-8-aza-bicyclo[3.2.1]oct-2-ene

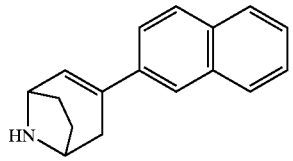

3-Hydroxy-3-naphthalen-2-yl-8-aza-bicyclo[3.2.1]octane-8-carboxylic acid tert-butyl ester (6.80 g, 19.3 mmol) and 10 mL TFA are stirred at 23° C. in 80 mL of $CH_2Cl_2$ for 2.5 h. The volatiles are removed and the residue partitioned between 100 mL of saturated $NaHCO_3$ and 100 mL EtOAc. The aqueous layer is extracted with 2×50 mL EtOAc, and the combined organics are washed with 3×50 mL $H_2O$, 1×50 mL brine, dried over $MgSO_4$, filtered, and stripped to give 4.50 g (19.1 mmol, a 100% yield) of the title compound as a white solid. MS (ES) m/z (relative intensity): 236 ($M^++H$, 100).

Step 4

4-[2-(3-Naphthalen-2-yl-8-aza-bicyclo[3.2.1]oct-2-en-8-yl)-ethoxy]-1H-indole

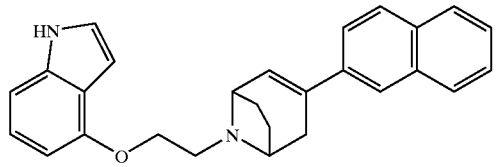

4-(2-Chloro-ethoxy)-1H-indole (170 mg, 0.87 mmol), 469 mg (1.74 mmol) of 3-naphthalen-2-yl-8-aza-bicyclo[3.2.1]oct-2-ene and 10 mL of DMSO are heated at 100° C. for 24 h. After cooling to 23° C., the orange reaction mixture is poured into 100 mL $H_2O$. Extraction with $CH_2Cl_2$ (2×50 mL), combining the organic layers and washing with $H_2O$ (4×50 mL), brine (1×50 mL), drying over $MgSO_4$, and evaporation gives an orange oil. Flash chromatography on $SiO_2$ gel, eluting with $CHCl_3$/MeOH (40/1 to 10/1), gives 216 mg (0.59 mmol, a 63% yield) of the title compound as an off-white solid. The corresponding oxalate salt is prepared by combining the title compound with 1 equiv. of oxalic acid in EtOH. A white solid precipitates. Recrystallization from EtOH/$Et_2O$ gives the oxalate salt of the title compound as an off-white solid. mp: 212-215° C.; MS (ES) m/z 395 $(MH)^+$.

EXAMPLE 2

3-{8-[2-(1H-Indol-4-yloxy)ethyl]-8-azabicyclo
[3.2.1]oct-2-en-3-yl}-1H-indole

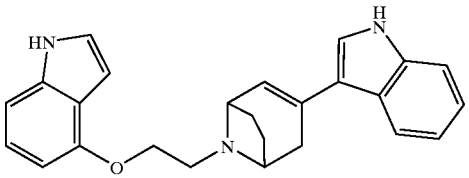

Step 1 tert-Butyl-3-{1-[tert-butyl(dimethyl)silyl]-1H-indol-3-yl}-3-hydroxy-8-azabicyclo[3.2.1]octane-8-carboxylate

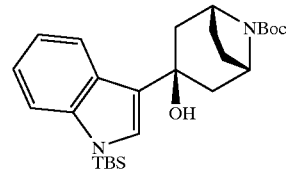

To 4.8 g (15.5 mmol) 3-bromo-1-(tert-butyl-dimethyl-silanyl)-1H-indole in 60 mL THF at −78° C. is added 19.1 mL (32.5 mmol) of a 1.7M solution of t-BuLi/pentane in drops over 10 min. After stirring at −78° C. for 30 min, 3.48 g (15.5 mmol) 3-oxo-8-aza-bicyclo[3.2.1]octane-8-carboxylic acid tert-butyl ester in 20 mL THF is added via a cannula over 5 min. After stirring at 23° C. for 3 h, the reaction mixture is poured into sat. aqueous $NaHCO_3$, and extracted with 2×50 mL EtOAc. The combined organics are washed with 1×100 mL $H_2O$, 1×100 mL brine, dried over $MgSO_4$, filtered and evaporated to an orange oil. Flash chromatography on $SiO_2$ gel, eluting with $CH_2Cl_2$/EtOAc (80/1 to 20/1), gives 3.74 g (8.2 mmol, a 53% yield) of the title compound as an off-white wax. MS (ES) m/z 457 $(MH)^+$.

Step 2

3-(8-Aza-bicyclo[3.2.1]oct-2-en-3-yl)-1H-indole

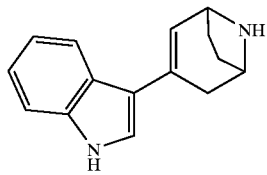

To 1.25 g (2.74 mmol) tert-butyl-3-{1-[tert-butyl (dimethyl)silyl]-1H-indol-3-yl}-3-hydroxy-8-azabicyclo [3.2.1]octane-8-carboxylate in 25 mL CH$_2$Cl$_2$ is added 6 mL of TFA. After stirring at 23° C. for 45 min, the reaction mixture is poured into sat. aqueous NaHCO$_3$ (300 mL) and extracted with 3×50 mL CH$_2$Cl$_2$. The combined organics are washed with 1×100 mL H$_2$O, 1×100 mL of brine, dried over Na$_2$SO$_4$, filtered and evaporated to give 603 mg (2.24 mmol, an 82% yield) of the title compound as a yellow/orange oil. MS (ES) m/z 269 (MH)$^+$.

Step 3

3-{8-[2-(1H-Indol-4-yloxy)ethyl]-8-azabicyclo [3.2.1]oct-2-en-3-yl}-1H-indole

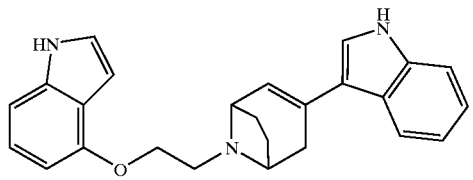

To 200 mg (0.89 mmol) 3-(8-aza-bicyclo[3.2.1]oct-2-en-3-yl)-1H-indole, 174 mg (0.89 mmol) 4-(2-chloroethoxy)-1H-indole and 10 mL MeCN is added 246 mg (1.78 mmol) K$_2$CO$_3$. After heating at 80° C. for 12 h, the reaction mixture is cooled to 23° C., filtered through celite and evaporated to a light yellow oil. Flash chromatography on SiO$_2$ gel, eluting with CHCl$_3$/MeOH (20/1 to 10/1), gives 208 mg (0.54 mmol, a 61% yield) of the title compound as an off-white solid. The corresponding oxalate salt is prepared by combining the title compound with 1 equivalent of oxalic acid in EtOH/Et$_2$O. The oxalate salt of the title compound precipitates as an off-white solid. Recrystallization from EtOH/Et$_2$O gives the oxalate salt of the title compound as an off-white solid. mp: 135–138° C.; MS (ES) m/z 384 (MH)$^+$.

EXAMPLE 3

2-[3-(1H-Indol-3-yl)-8-azabicyclo[3.2.1]oct-2-en-8-yl]ethyl 5-quinolinyl Ether

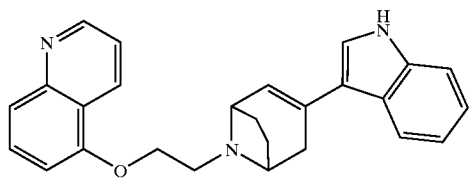

Step 1

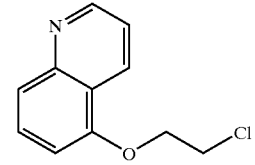

5-(2-Chloro-ethoxy)-quinoline

The title compound is prepared according to the procedure for Example 1, Step 1 except that 5-hydroxyquinoline is used in place of 4-hydroxyindole. Yield: 41%; MS (ES) m/z 208 (MH)$^+$.

Step 2

2-[3-(1H-Indol-3-yl)-8-azabicyclo[3.2.1]oct-2-en-8-yl]ethyl 5-quinolinyl Ether

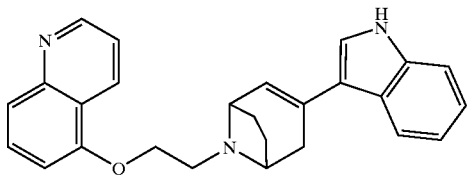

The title compound is prepared according to the procedure of Example 2, Step 3 except that 5-(2-chloro-ethoxy)-quinoline is used in place of 4-(2-chloro-ethoxy)-1H-indole. Yield: 59%. The corresponding oxalate salt is prepared by combining the title compound with 1 equiv. of oxalic acid in EtOH/Et$_2$O. The oxalate salt of the title compound precipitates as an off-white solid. Recrystallization from EtOH/Et$_2$O gives the oxalate salt of the title compound as an off-white solid. mp: 91–93° C. (dec.); MS (ES) m/z 396 (MH)$^+$.

EXAMPLE 4

8-[2-(2,3-Dihydro-benzo[1,4]dioxin-5-yloxy)-ethyl]-3-naphthalen-2-yl-8-aza-bicyclo[3.2.1]oct-2-ene

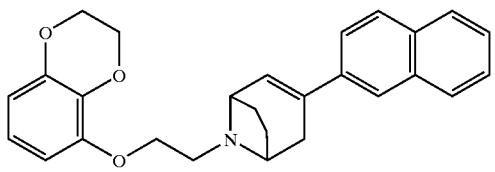

Step 1

5-(2-Chloro-ethoxy)-2,3-dihydro-benzo[1,4]dioxine

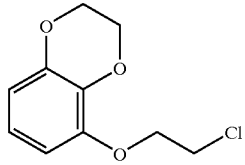

The title compound is prepared according to the procedure for Example 1, Step 1 except that 8-hydroxybenzodioxane is used instead of 4-hydroxyindole. Yield: 41%; MS (CI) m/z 215 (MH)$^+$.

Step 2

8-[2-(2,3-Dihydro-benzo[1,4]dioxin-5-yloxy)-ethyl]-3-naphthalen-2-yl-8-aza-bicyclo[3.2.1]oct-2-ene

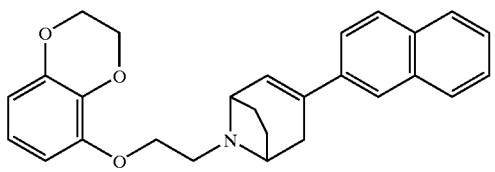

The title compound is prepared according to the procedure of Example 2, Step 3 except that 5-(2-chloro-ethoxy)-2,3-dihydro-benzo[1,4]dioxine is used in place of 4-(2-chloro-ethoxy)-1H-indole. Yield: 70%. The corresponding oxalate salt is prepared by combining the title compound with 1 equivalent of oxalic acid in EtOH. The oxalate salt of the title compound precipitates as an off-white solid. mp: 151-153° C. (dec.); MS (ES) m/z 414 (MH)$^+$.

EXAMPLE 5

6-Methoxy-N-(2-[3-(2-naphthyl)-8-azabicyclo[3.2.1]oct-2-en-8-yl]ethyl}-8-quinolinamine

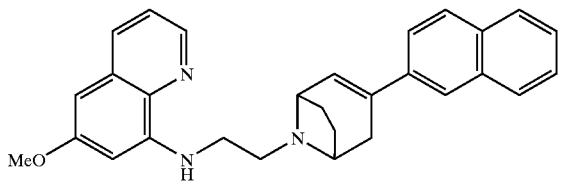

Step 1 tert-Butyl 2-[3-(2-naphthyl)-8-azabicyclo[3.2.1]oct-2-en-8-yl]ethylcarbamate

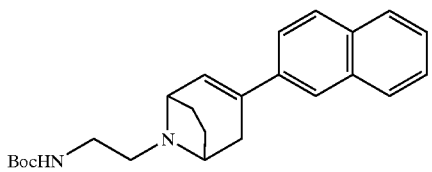

3-Naphthalen-2-yl-8-aza-bicyclo[3.2.1]oct-2-ene (1.0 g, 4.25 mmol), 0.84 g (4.68 mmol) tert-butyl 2-chloroethylcarbamate, and 1.80 g (12.8 mmol) K$_2$CO$_3$ are stirred at 80 C in 8 mL DMF for 10 h. The reaction mixture is poured into 100 mL H$_2$O and extracted with 3×50 mL EtOAc. The combined organics are washed with 3×100 mL H$_2$O, 1×100 mL brine, dried over MgSO$_4$, filtered, and the volatiles are evaporated. Flash chromatography of the crude product on SiO$_2$ gel (gradient of EtOAc to EtOAc:2M NH$_3$ in MeOH 10:1) gives 0.96 g (2.54 mmol, a 60% yield) of the title compound as a yellow solid. mp: 105 C; MS (ES) m/z 379 (MH)$^+$.

Step 2

2-[3-(2-Naphthyl)-8-azabicyclo[3.2.1]oct-2-en-8-yl]ethylamine

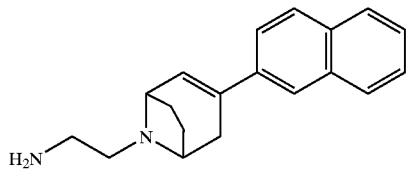

tert-Butyl 2-[3-(2-naphthyl)-8-azabicyclo[3.2.1]oct-2-en-8-yl]ethylcarbamate (0.50 g, 1.30 mmol) and 1 mL trifluoroacetic acid are stirred at 23 C in 20 mL CH$_2$Cl$_2$ for 2 h. The volatiles are evaporated, and the residue is partitioned between 50 mL of saturated aqueous NaHCO$_3$ and 50 mL EtOAc. The aqueous layer is extracted with 2×25 mL EtOAc, and the combined organics are washed with 3×50 mL H$_2$O, 1×50 mL brine, dried over MgSO$_4$, filtered, and evaporated to give 0.22g (0.79 mmol, a 60% yield) of the title compound as an orange solid. mp: 62-65 C; MS (ES) m/z 279 (MH)$^+$.

Step 3

6-Methoxy-8-nitroquinoline

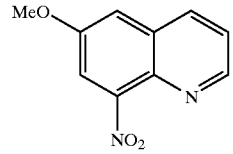

4-Methoxy-2-nitroaniline (20.0 g, 119 mmol), 34.0 g (369 mmol) glycerol, 24.0 g (107 mmol) 3-nitrobenzensulfonic acid sodium salt, 25 mL H$_2$O and 34 mL H$_2$SO$_4$ are refluxed for 12 h. The reaction mixture is cooled to 45° C., poured into 1 L of cold H$_2$O and vigorously stirred with 500 mL of CH$_2$Cl$_2$ for 30 min. The resulting bi-phasic solution is filtered through celite, and the aqueous layer is extracted with 3×300 mL CH$_2$Cl$_2$. The combined organics are washed with 1×400 mL H$_2$O, 1×400 mL brine, dried over MgSO$_4$, filtered, and the volatiles are evaporated. Flash chromatography of the crude product on SiO$_2$ gel, eluting with hexanes/EtOAc (4/1), gives 10.0 g (49.0 mmol, a 42% yield) of the title compound as a tan solid. MS (ES) m/z 205 (MH)$^+$.

Step 4

6-Methoxy-quinolin-8-ylamine

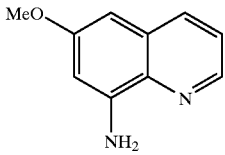

A mixture of 9.20 g (45.1 mmol) 6-methoxy-8-nitroquinoline, 1.8 g of 10% Pd/C and 150 mL THF is placed under 40 psi of $H_2$ and shaken in a Parr reactor at 23° C. for 4 h. The Pd/C is removed via filtration through celite, and the solvent evaporated. Flash chromatography on $SiO_2$ gel, eluting with hexanes/EtOAc (1/1 to 1/3), gives 7.40 g (42.5 mmol, a 95% yield) of the title compound as an off-white solid. MS (ES) m/z 175 (MH)$^+$.

Step 5

8-Bromo-6-methoxyquinoline

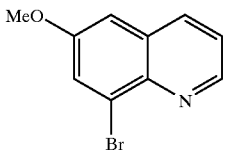

To 5.05 g (29.0 mmol) 6-methoxy-quinolin-8-yl-amine in 25 mL of 48% HBr at 0° C. is added a solution of 2.60 g (37.7 mmol) and 20 mL $H_2O$. After stirring at 0° C. for 15 min, the resulting mixture is added dropwise to a 75° C. solution of 5.0 g (34.8 mmol) CuBr and 60 mL of 48% HBr. After 5.5 h, the reaction mixture is neutralized with 150 mL of ice cold 5N NaOH, the resulting mixture is stirred with 300 mL EtOAc and filtered through a pad of celite. This mixture is extracted 2×100 mL EtOAc, and the combined organics are washed with 1×200 mL $H_2O$, 1×200 mL brine, dried over $Na_2SO_4$, filtered, and the volatiles are evaporated. Flash chromatography on $SiO_2$ gel, eluting with hexanes/EtOAc (4/1 to 1/1), gives 4.23 g (17.8 mmol, a 61% yield) of the title compound as a brown oil. MS (ES) m/z 239 (MH)$^+$.

Step 6

6-Methoxy-N-{2-[3-(2-naphthyl)-8-azabicyclo [3.2.1]oct-2-en-8-yl]ethyl}-8-quinolinamine

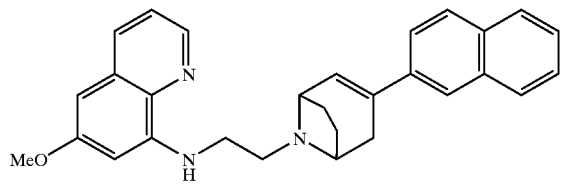

A mixture of 0.17 g, (0.61 mmol) 2-[3-(2-naphthyl)-8-azabicyclo[3.2.1]oct-2-en-8-yl]ethylamine, 0.13 g (0.55 mmol) 8-bromo-6-methoxyquinoline, 30 mg (0.03 mmol) $Pd_2(dba)_3$, 20 mg (0.08 mmol) 2-(di-t-butylphosphino) biphenyl and 10 mL PhMe is stirred at 23° C. for 16 h. The reaction mixture is poured into 100 mL of $H_2O$ and extracted 3×50 mL EtOAc. The combined organics are washed with 1×100 mL $H_2O$, 1×100 mL brine, dried over $MgSO_4$, filtered, and the volatiles are evaporated. The crude product is subjected to flash chromatography on $SiO_2$, eluting with EtOAc to EtOAc/2M $NH_3$ in MeOH (40/1), to give the title compound as an off-white solid. This solid is dissolved in 4 mL of absolute EtOH and treated with 0.01 g (0.14 mmol) $(CO_2H)_2$ to give 0.07 g (0.13 mmol, a 23% yield) of the oxalate salt of the title compound as a dark green solid: mp: 179-182 C; MS (ES) m/z 436 (MH)$^+$.

EXAMPLE 6

6-Chloro-N-{2-[3-(2-naphthyl)-8-azabicyclo[3.2.1] oct-2-en-8:yl]ethyl}-8-quinolinamine

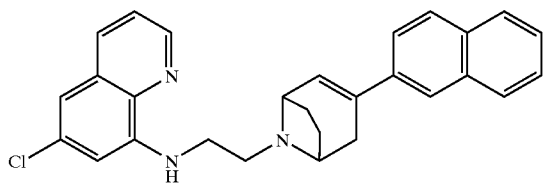

Step 1

6-Chloro-8-nitroquinoline

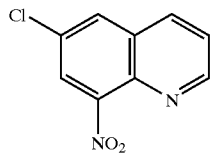

6-Chloro-8-nitroquinoline is made by the method described for Example 5, Step 3, where 4-chloro-2-nitroaniline is used in place of 4-methoxy-2-nitroaniline. Yield: 42% of tan needles; mp: 149–155° C.; MS (ES) m/z 209 (MH)$^+$.

Step 2

6-Chloro-quinolin-8-ylamine

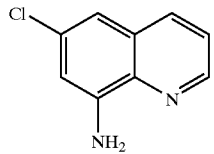

To a solution of 6.30 g (30.3 mmol) 6-chloro-8-nitroquinoline, 14.7 g (272 mmol) $NH_4Cl$, 120 mL $H_2O$ and 250 mL EtOH is added 5.0 g (90.6 mmol) Fe powder, and the resulting mixture is refluxed for 2.5 h. The volatiles are evaporated, and the residue is stirred in mixture of 200 mL $CH_2Cl_2$ and 300 mL water for 30 min. The resulting bi-phasic solution is filtered through celite, the layers are separated, and the aqueous layer is extracted 2×100 mL $CH_2Cl_2$. The combined organics are washed with 1×100 mL $H_2O$, 1×100 mL brine, dried over $MgSO_4$, filtered, and the volatiles are evaporated. Flash chromatography on $SiO_2$, eluting with hexanes/EtOAC (10/1 to 4/1), gives 2.80 g (15.7 mmol, a 52% yield) of the title compound as a tan solid. mp: 70–73° C.; MS (ES) m/z 179 (MH)+.

Step 3

8-Bromo-6-chloroquinoline

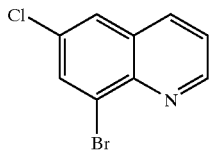

8-Bromo-6-chloroquinoline is synthesized by the method described for Example 5, Step 5, where 6-chloro-quinolin-8-ylamine is used in place of 6-methoxy-quinolin-8-ylamine. Yield: 77% yield of a tan solid. MS (ES) m/z 243 (MH)+.

Step 4

6-Chloro-N-{2-[3-(2-naphthyl)-8-azabicyclo[3.2.1]oct-2-en-8-yl]ethyl}-8-quinolinamine

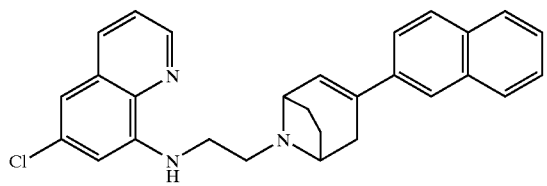

6-Chloro-N-{2-[3-(2-naphthyl)-8-azabicyclo[3.2.1]oct-2-en-8-yl]ethyl}-8-quinolinamine is synthesized by the method described for Example 5, Step 6, where 8-bromo-6-chloroquinoline is used in place of 8-bromo-6-methoxyquinoline and BINAP is used in place of 2-(di-t-butylphosphino)biphenyl. The oxalate salt of the title compound, a tan solid prepared in 60% yield, is prepared as in Example 5, Step 6. mp: 205–206° C.; MS (ES) m/z 441 (MH)+.

EXAMPLE 7

N-{2-[3-(2-Naphthyl)-8-azabicyclo[3.2.1]oct-2-en-8-yl]ethyl}-8-quinolinamine

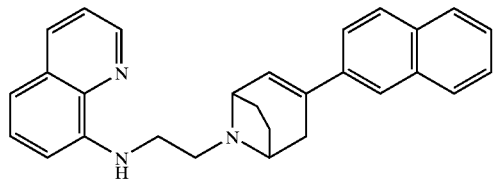

N-{2-[3-(2-Naphthyl)-8-azabicyclo[3.2.1]oct-2-en-8-yl]ethyl}-8-quinolin-amine is prepared by the method described for Example 5, Step 6, where 8-bromo-6-chloroquinoline is used in place of 8-bromo-6-methoxyquinoline and BINAP is used in place of 2-(di-t-butylphosphino)biphenyl. The oxalate of the title compound, a yellow solid prepared in 49% yield, is synthesized as in Example 5, Step 6. mp: 199–200 C; MS (ES) m/z 406 (MH)+.

EXAMPLE 8

6-Methoxy-8-[2-(3-naphthalen-2-yl-8-azabicyclo[3.2.1]oct-2-en-8-yl)-ethoxy]-quinoline

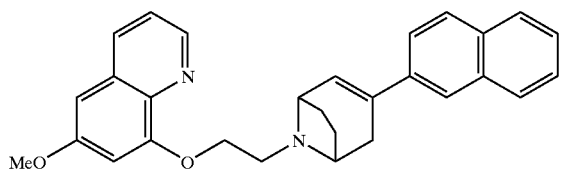

Step 1

2-[3-(2-Naphthyl)-8-azabicyclo[3.2.1]oct-2-en-8-yl]ethanol

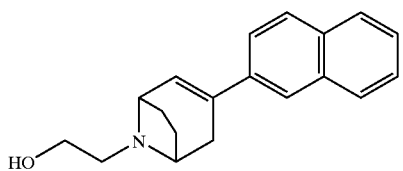

3-Naphthalen-2-yl-8-aza-bicyclo[3.2.1]oct-2-ene (1.00 g, 4.25 mmol), 1.05 g (8.40 mmol) 2-bromoethanol, 1.70 g (12.6 mmol) K$_2$CO$_3$ and 57 mL of DMF are stirred at 80 C for 12 h. The reaction mixture is poured into 300 mL of cold H$_2$O and extracted with 3×50 mL of EtOAc. The combined organics are washed with 3×100 mL of H$_2$O, 1×100 mL of brine, dried over MgSO$_4$, filtered, and the volatiles are evaporated to give 1.08 g (3.87 mmol, a 91% yield) of the title compound as a white solid. mp: 113–114° C.; MS (ES) m/z 280 (MH)+.

Step 2

8-(2-Chloroethyl)-3-(2-naphthyl)-8-azabicyclo[3.2.1]oct-2-ene

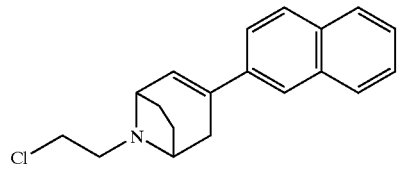

2-[3-(2-Naphthyl)-8-azabicyclo[3.2.1]oct-2-en-8-yl]ethanol (0.95 g, 3.40 mmol), 0.42 g (3.70 mmol) MsCl, 0.71 mL (515 mg, 5.10 mmol) Et$_3$N and 20 mL CH$_2$Cl$_2$ are stirred at 23 C in for 12 h. The reaction mixture is poured into 200 mL of H$_2$O and extracted with 3×50 mL CH$_2$Cl$_2$. The combined organics are washed with H$_2$O (3×100 mL,) brine (1×100 mL), dried over MgSO$_4$, filtered, and the volatiles are evaporated. Flash chromatography on SiO$_2$ gel, eluting with EtOAc/MeOH (20/1 to 10/1), gives 0.50 g (1.68 mmol, a 50% yield) of the title compound as a tan solid. mp: 122–123° C.; MS (ES) m/z 298 (MH)+.

Step 3

6,8-Dimethoxyquinoline

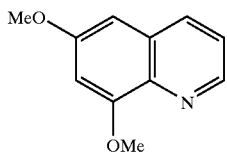

2,4-Dimethoxyaniline (20.0 g, 131 mmol), 8.70 mL (7.30 g, 131 mmol) acrolein and 500 mL 1 N HCl are refluxed for 30 min. The reaction mixture is cooled to 23° C., poured into 200 mL of vigorously stirring EtOAc, and neutralized with 10N NaOH. The resulting bi-phasic solution is stirred for 30 min and filtered through celite. The layers are separated, and the aqueous layer is extracted with 3×300 mL EtOAc. The combined organics are washed with 1×400 mL $H_2O$, 1×400 mL brine, dried over $MgSO_4$, filtered, and the volatiles are evaporated. Flash chromatography on $SiO_2$, eluting with 4/1 EtOAc/hexanes containing 10% MeOH, gives 6.40 g (33.8 mmol, a 26% yield) of the title compound as an off-white solid. MS (ES) m/z 190 $(MH)^+$.

Step 4

6-Methoxyquinolin-8-ol

To a −25° C. solution of 3.0 g (15.9 mmol) 6,8-dimethoxyquinoline and 160 mL $CH_2Cl_2$ is added 16 mL (15.9 mmol) of 1M $BBr_3$ in $CH_2Cl_2$. After stirring for 2 h at −25° C., the reaction mixture is quenched with 300 mL of $H_2O$, the layers separated in a separatory funnel, and the aqueous extracted with $CH_2Cl_2$ (2×100 mL). The combined organics are washed with 1×100 mL $H_2O$, 1×100 mL brine, dried over $MgSO_4$, filtered, and the volatiles are evaporated. Flash chromatography on $SiO_2$, eluting with 3/1 EtOAc/hexanes containing 10% MeOH, gives 0.96 g (5.48 mmol, a 34% yield) of the title compound as an tan solid. MS (ES) m/z 176 $(MH)^+$.

Step 5

6-Methoxy-8-[2-(3-naphthalen-2-yl-8-azabicyclo [3.2.1]oct-2-en-8-yl)-ethoxy]-quinoline

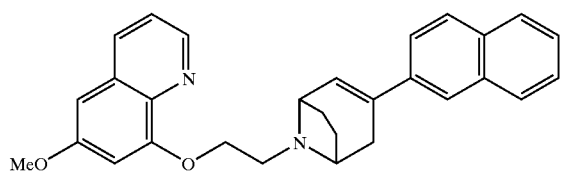

8-(2-Chloroethyl)-3-(2-naphthyl)-8-azabicyclo[3.2.1]oct-2-ene (0.50 g, 1.70 mmol), 0.39 g (2.20 mmol) 6-methoxyquinolin-8-ol, 0.08 g (2.00 mmol) NaH (60% dispersion in mineral oil) and 3 mL DMSO are stirred at 50 C for 16 h. The reaction mixture is poured into 100 mL of $H_2O$ and extracted with 3×50 mL EtOAc. The combined organics are washed with 3×100 mL $H_2O$, 1×100 mL brine, dried over $MgSO_4$, filtered, and the volatiles are evaporated. The crude product is subjected to flash chromatography on $SiO_2$ gel, eluting with EtOAc and then 40/1 EtOAc/2M $NH_3$ in MeOH, to produce an off-white solid. This solid is treated with 0.06 g (0.67 mmol) $(CO_2H)_2$ in 4 mL of absolute EtOH to give 0.33 g (0.13 mmol, a 38% yield) of the oxalate salt of the title compound as a white solid. mp: 100–103° C.; MS (ES) m/z 437 $(MH)^+$.

EXAMPLE 9

8-[2-(Indan-4-yloxy)-ethyl]-3-naphthalen-2-yl-8-azabicyclo[3.2.1]oct-2-ene

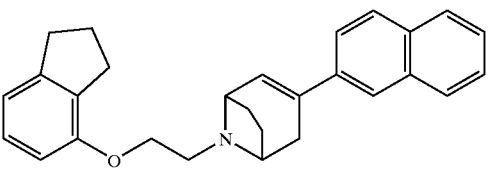

Step 1

4-(2-Chloroethoxy)-indan

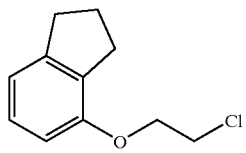

4-(2-Chloroethoxy)-indan is made by the method described for Example 1, Step 1 where 4-indanol is used in place of 4-(2-chloro-ethoxy)-1H-indole Yield: 53% yield of a pale yellow oil. MS (ES) m/z 197 $(MH)^+$.

Step 2

8-[2Indan-4-yloxy)-ethyl]-3-naphthalen-2-yl-8-azabicyclo[3.2.1]oct-2-ene

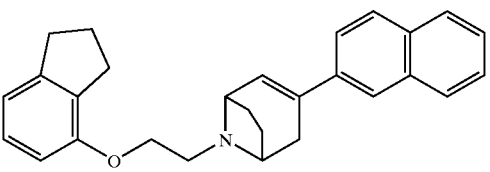

The title compound is prepared according to the procedure of Example 1, Step 4, except that 4-(2-chloroethoxy)-indan is used in place of 4-(2-chloro-ethoxy)-1H-indole. The oxalate salt of the title compound is prepared by treating the title compound with 1 equivalent of oxalic acid in EtOH. Yield: 37% yield of a white solid. mp: 172–174° C.; MS (ES) m/z 396 $(MH)^+$.

EXAMPLE 10

4-{2-[3-(6-Methoxy-naphthalen-2-yl)-8-aza-bicyclo[3.2.1]oct-2-en-8-yl]-ethoxy}-1H-indole

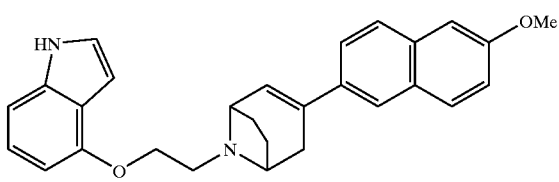

Step 1

3-Hydroxy-3-(6-methoxy-naphthalen-2-yl)-8-aza-bicyclo[3.2.1]octane-8-carboxylic Acid Tert-Butyl Ester

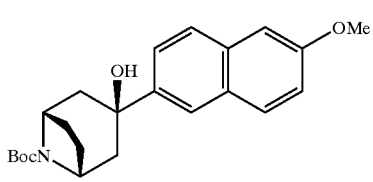

The title compound is prepared according to the procedure of Example 1, Step 2, except that 2-bromo-6-methoxy-naphthalene is used in place of 2-bromonaphthalene. Yield: 43%; MS (ES) m/z 384 (MH)$^+$.

Step 2

3-(6-Methoxy-naphthalen-2-yl)-8-aza-bicyclo[3.2.1]oct-2-ene

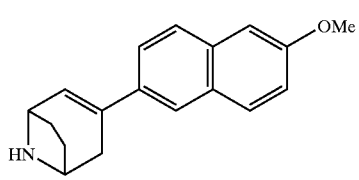

The title compound is prepared according to the procedure of Example 1, Step 3, except that 3-hydroxy-3-(6-methoxy-naphthalen-2-yl)-8-aza-bicyclo[3.2.1]octane-8-carboxylic acid tert-butyl ester is used in place of 3-hydroxy-3-naphthalen-2-yl-8-aza-bicyclo[3.2.1]octane-8-carboxylic acid tert-butyl ester. Yield 85%; mp: 138° C.; MS (ES) m/z 266 (MH)$^+$.

Step 3

4-{2-[3-(6-Methoxy-naphthalen-2-yl)-8-aza-bicyclo[3.2.1]oct-2-en-8-yl]-ethoxy}-1H-indole

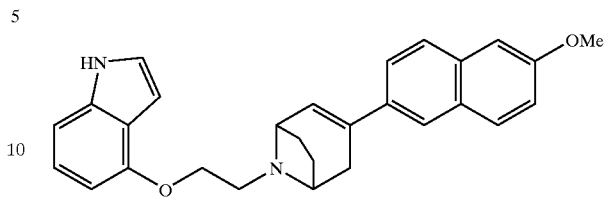

The title compound is prepared according to the procedure of Example 1, Step 4 except that 3-(6-methoxy-naphthalen-2-yl)-8-aza-bicyclo[3.2.1]oct-2-ene is used in place of 3-naphthalen-2-yl-8-aza-bicyclo[3.2.1]oct-2-ene. Yield: 44%. The oxalate salt of the title compound is prepared by treating the title compound with 1 equiv. of oxalic acid in EtOH/Et$_2$O. mp: 130–132° C. (dec.); MS (ES) m/z 425 (MH)$^+$.

EXAMPLE 11

3-Naphthalen-2-yl-8-[2-(3-trifluoromethyl-phenoxy)-ethyl]-8-aza-bicyclo[3.2.1]oct-2-ene

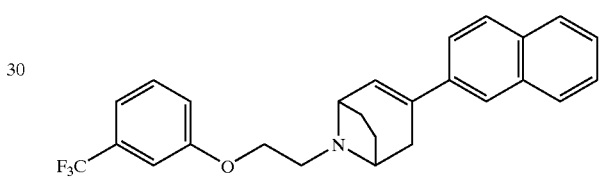

Step 1

1-(2-Chloro-ethoxy)-3-trifluoromethyl-benzene

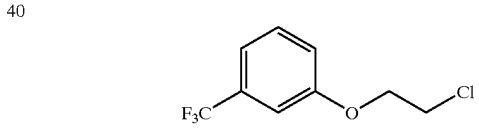

The title compound is prepared according to the procedure of Example 1, Step 1, except that 3-trifluoromethylphenol is used in place of 4-hydroxyindole. Yield: 99%; MS (Cl) m/z 225 (MH)$^+$.

Step 2

3-Naphthalen-2-yl-8-[2-(3-trifluoromethyl-phenoxy)-ethyl]-8-aza-bicyclo[3.2.1]oct-2-ene

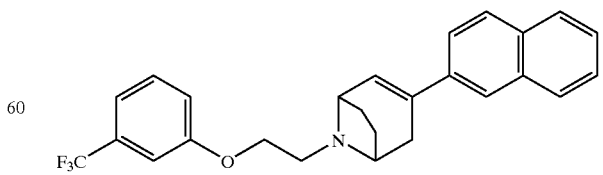

The title compound is prepared according to the procedure of Example 1, Step 4 except that 1-(2-chloro-ethoxy)-3-trifluoromethyl-benzene is used in place 4-(2-chloroethoxy)-1H-indole. Yield: 33%. The oxalate salt of the title compound is prepared by treating the title compound with 1 equiv. of oxalic acid in EtOH. mp: 128–130° C. (dec.); MS (ES) m/z 424 (MH)+.

EXAMPLE 12

4-[2-(3-Naphthalen-2-yl-8-aza-bicyclo[3.2.1]oct-8-yl)-ethoxy]-1H-indole

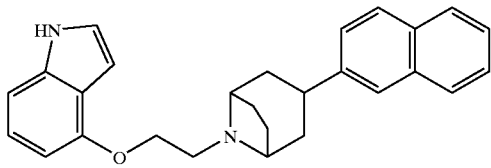

Step 1

3-(2-Naphthyl)-8-azabicyclo[3.2.1]octane

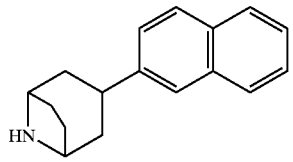

To 313 mg (1.33 mmol) 3-naphthalen-2-yl-8-aza-bicyclo[3.2.1]oct-2-ene in 10 mL EtOAc is added 100 mg of 10% Pd/C. This mixture is placed under 40 psi of $H_2$ and shaken in a Parr hydrogenator for 47 h. The resulting mixture is then filtered through celite and evaporated to give 197 mg (0.83 mmol, a 62% yield) of the title compound as a white solid. mp: 189–194° C.; MS (ES) m/z 238 (MH)+.

Step 2

4-[2-(3-Naphthalen-2-yl-8-aza-bicyclo[3.2.1]oct-8-yl)-ethoxy]-1H-indole

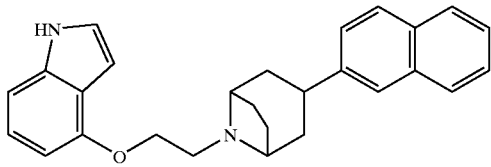

The title compound is prepared according to the procedure of Example 1, Step 4 except that 3-(2-naphthyl)-8-azabicyclo[3.2.1]octane is used in place of 3-naphthalen-2-yl-8-aza-bicyclo[3.2.1]oct-2-ene. Yield: 36%. The corresponding oxalate salt is prepared by treating the title compound with 1 equiv. of oxalic acid in EtOH. mp: 119–120° C. (dec.); MS (ES) m/z 397 (MH)+.

EXAMPLE 13

4-{2-[3-(3,4-Dichloro-phenyl)-8-aza-bicyclo[3.2.1]oct-2-en-8-yl]-ethoxy}-1H-indole

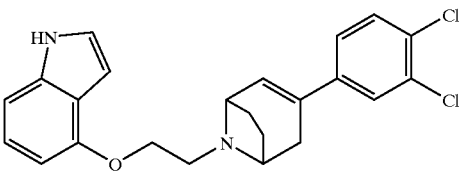

Step 1

3-(3,4-Dichloro-phenyl)-8-methyl-8-aza-bicyclo[3.2.1]octan-3-ol

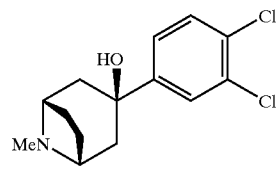

To 4.0 mL (7.04 g, 31.18 mmol) 4-bromo-1,2-dichloro-benzene in 100 mL THF at −78° C. is added 12.47 mL of a 2.5 M solution of n-BuLi in hexanes in drops over 5 min. After stirring at −78° C. for 45 min, 4.34 g (31.18 mmol) tropinone is added as a solid. The resulting mixture is warmed to 23° C. and stirred for 18 h. After pouring into 2.5 N NaOH, the reaction mixture is extracted with 2×100 mL EtOAc, the organics are combined and washed with 1×100 mL $H_2O$, 1×100 mL brine, dried over $MgSO_4$, filtered and evaporated to an off-white solid. Flash chromatography on $SiO_2$ gel, eluting with $CHCl_3$/MeOH (20/1 to 5/1), gives 2.58 g (9.02 mmol, a 28% yield) of the title compound as a white solid. mp: 153–154° C.; MS (ES) m/z 287 (MH)+.

Step 2

3-(3,4-Dichloro-phenyl)-8-methyl-8-aza-bicyclo[3.2.1]oct-2-ene

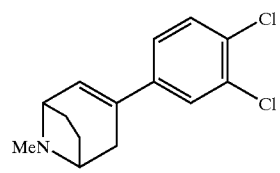

To 2.35 g (8.76 mmol) of 3-(3,4-dichloro-phenyl)-8-methyl-8-aza-bicyclo[3.2.1]octan-3-ol in 50 mL of $Cl(CH_2)_2Cl$ is added 1.92 mL (3.13 g, 26.67 mmol) $SOCl_2$. After stirring at 23 C for 17 h, the reaction mixture is poured into 5 N NaOH, extracted with 1×100 mL $H_2O$, 1×100 mL brine, dried over $MgSO_4$, filtered and extracted to give a brown oil. Flash chromatography on $SiO_2$, eluting with $CHCl_3$/MeOH (40/1 to 10/1) gives 1.24 g (4.62 mmol, a 53% yield) of the title compound as an orange oil. MS (ES) m/z 269 (MH)+.

Step 3

3-(3,4-Dichloro-phenyl)-8-aza-bicyclo[3.2.1]oct-2-ene

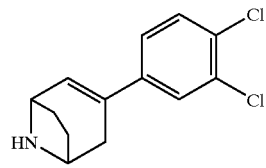

To 1.08 g (4.03 mmol) 3-(3,4-dichloro-phenyl)-8-methyl-8-aza-bicyclo[3.2.1]oct-2-ene in 20 mL Cl(CH$_2$)$_2$Cl is added 1.31 mL (1.73 g, 12.08 mmol) of 1-chloroethyl chloroformate, and the resulting mixture is heated to reflux for 24 h. Evaporation of all volatiles gives an orange oil which is dissolved in methanol (20 mL) and heated to reflux for 1 h. Evaporation of all volatiles yielded an orange solid which is dissolved in 100 H$_2$O and treated with 50 mL of 2.5 N NaOH. Extraction with 3×25 mL CH$_2$Cl$_2$, combining the organics and washing with 1×50 mL H$_2$O, 1×50 mL brine, drying over MgSO$_4$, filtering and evaporation a dark orange oil. Flash chromatography on SiO$_2$ gel, eluting with EtOAc, then 10/1 EtOAc/2.0M NH$_3$ in MeOH), gives 511 mg (2.01 mmol, a 50% yield) of the title compound as an orange solid. The oxalate salt of the title compound may be prepared by combining the title compound with 1 equiv. of oxalic acid in EtOH. A white solid precipitates. mp: 185–186° C. MS (ES) m/z 255 (MH)$^+$.

Step 4

4-{2-[3-(3,4-Dichloro-phenyl)-8-aza-bicyclo[3.2.1]oct-2-en-8-yl]-ethoxy}-1H-indole

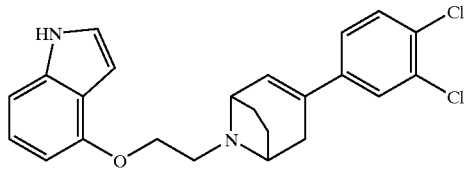

The title compound is prepared according to the procedure of Example 1, Step 4 except that 3-(3,4-dichloro-phenyl)-8-aza-bicyclo[3.2.1]oct-2-ene is used in place of 3-naphthalen-2-yl-8-aza-bicyclo[3.2.1]oct-2-ene. Yield: 44%. The corresponding oxalate salt is prepared by treating the title compound with 1 equiv. of oxalic acid in EtOH/Et$_2$O. mp: 120–123° C. (dec.); MS (ES) m/z 414 (MH)$^+$.

EXAMPLE 14

3-{8-[3-(1H-Indol-4-yloxy)propyl]-8-azabicyclo[3.2.1]oct-2-en-3-yl}-1H-indole

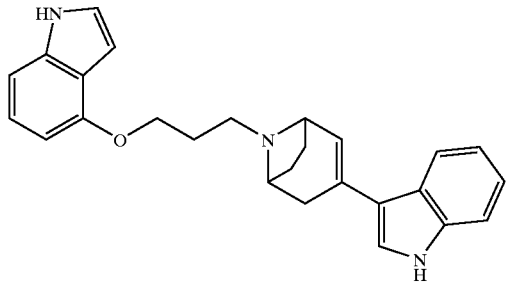

Step 1

4-(3-Chloropropoxy)-1H-indole

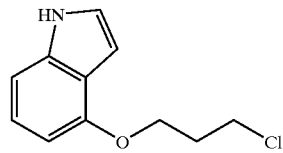

The title compound is prepared by the method described for Example 1, Step 1, where 2-chloropropanol is used in place of 2-chloroethanol Yield: 17% yield of a pale colorless wax. MS (ES) m/z 210 (MH)$^+$.

Step 2

3-{8-[3-(1H-Indol-4-yloxy)propyl]-8-azabicyclo[3.2.1]oct-2-en-3-yl}-1H-indole

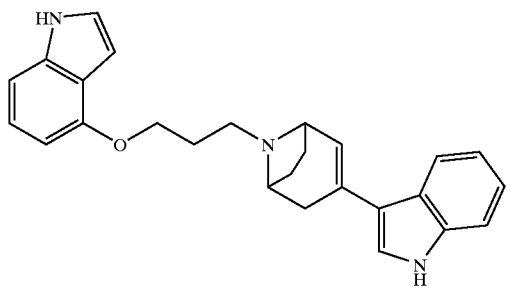

The title compound is prepared according to the procedure for Example 2, Step 3, except that 4-(3-chloropropoxy)-1H-indole is used in place of 4-(2-chloroethoxy)-1H-indole. Yield: 67% of a yellow gum. The corresponding oxalate salt is prepared by treating the title compound with 1 equiv. of oxalic acid in EtOH. mp: 182–184° C., MS (ES) m/z 398 (MH)$^+$.

EXAMPLE 15

4-[3-(3-Naphthalen-2-yl-8-aza-bicyclo[3.2.1]oct-2-en-8-yl)-propoxy]-1H-indole

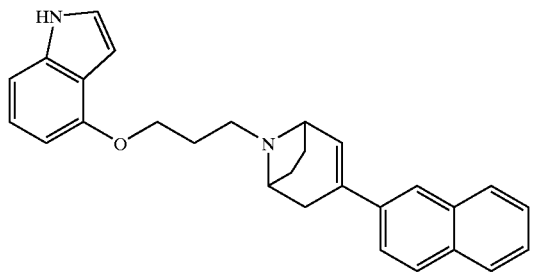

The title compound is prepared according to the procedure of Example 2, Step 3, except that 4-(3-chloropropoxy)-1H-indole is used in place of 4-(2-chloro-ethoxy)-1H-indole and 3-naphthalen-2-yl-8-aza-bicyclo[3.2.1]oct-2-ene is used in place of 3-(8-aza-bicyclo[3.2.1]oct-2-en-3-yl)-1H-indole. The corresponding oxalate salt is prepared by treating the title compound with 1 equiv. of oxalic acid in EtOH. Yield: 35% of a white solid. mp: 118–123° C.; MS (ES) m/z: 409.3 (MH)+.

EXAMPLE 16

4-{3-[3-(3,4-Dichlorophenyl)-8-azabicyclo[3.2.1]oct-2-en-8-yl]propoxy-1H-indole

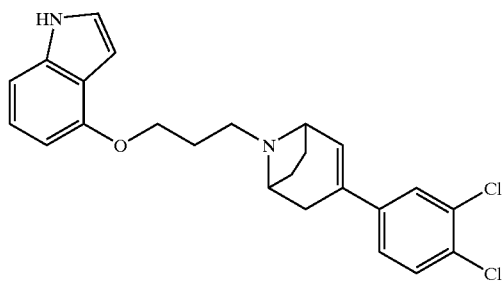

The title compound is prepared according to the procedure of Example 2, Step 3, except that 4-(3-chloropropoxy)-1H-indole is used in place of 4-(2-chloro-ethoxy)-1H-indole and 3-(3,4-dichloro-phenyl)-8-aza-bicyclo[3.2.1]oct-2-ene is used in place of 3-(8-aza-bicyclo[3.2.1]oct-2-en-3-yl)-1H-indole. The corresponding oxalate salt is prepared by treating the title compound with 1 equiv. of oxalic acid in EtOH. Yield: 22% of an off-white solid. mp: 150–153° C.; MS (ES) m/z: 427.2 (MH)+.

EXAMPLE 17

8-{2-[3-(2-Naphthyl)-8-azabicyclo[3.2.1]oct-8-yl]ethoxy}quinoline

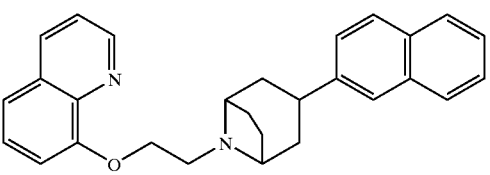

Step 1

2-[3-(2-Naphthyl)-8-azabicyclo[3.2.1]oct-8-yl]ethanol

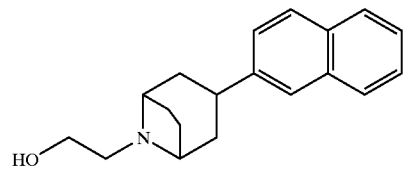

The title compound is prepared according to Example 8, Step 1, except that 3-(2-naphthyl)-8-azabicyclo[3.2.1]octane is used in place 3-naphthalen-2-yl-8-aza-bicyclo[3.2.1]oct-2-ene. Yield: 70%; mp: 84–88° C.; MS (ES) m/z: 282 (MH)+.

Step 2

8-(2-Chloroethyl)-3-(2-naphthyl)-8-azabicyclo[3.2.1]octane

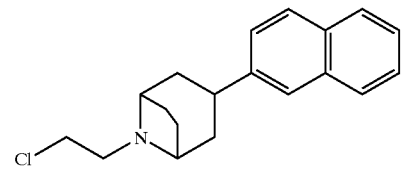

The title compound is prepared according to Example 8, Step 2, except that 2-[3-(2-naphthyl)-8-azabicyclo[3.2.1]oct-8-yl]ethanol is used in place of 2-[3-(2-naphthyl)-8-azabicyclo[3.2.1]oct-2-en-8-yl]ethanol. Yield: 91%; mp: 84–88° C.; MS (ES) m/z: 300 (MH)+.

Step 3

8-{2-[3-(2-Naphthyl)-8-azabicyclo[3.2.1]oct-8-yl]ethoxy}quinoline

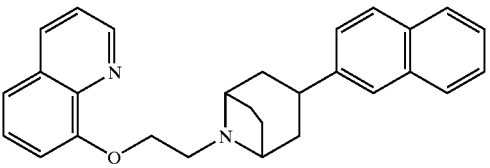

The title compound is prepared according to Example 8, Step 5, except 8-hydroxyquinoline is used in place 6-methoxyquinolin-8-ol. The corresponding oxalate salt is prepared by treating the title compound with 1 equiv. oxalic acid in DMF to precipitate a white solid. Yield: 51%; mp: 110–113° C.; MS (ES) m/z: 409 (MH)⁺.

EXAMPLE 18

8-({2-[3-(2-Naphthyl)-8-azabicyclo[3.2.1]oct-8-yl]ethyl}sulfanyl)quinoline

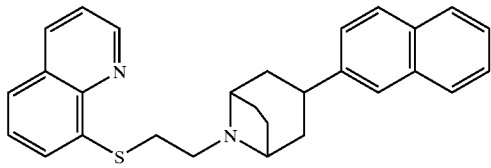

Step 1

8-Quinolinethiol

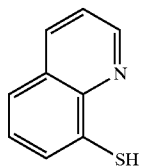

To a −78° C. solution of 2.37 g (11.1 mmol) 8-bromoquinoline in 20 mL diethyl ether (anhyd.) is added 4.4 mL (11 mmol) of n-BuLi (2.5 M in hexanes) in drops over 5 min. After 15 min, a suspension of 710 mg (22.2 mmol) of elemental sulfur in 15 mL benzene (anhyd.) is added in drops over 10 min, and then allowed to warm to 23° C. After 21 h, the mixture is poured into 200 mL 2 N NaOH, and the aqueous layer is extracted with $CH_2Cl_2$ (4×50 mL). The combined organics are washed with $H_2O$ (1×150 mL), brine (2×150 mL), dried over $MgSO_4$, filtered, and evaporated to an oil. The crude material was purified by flash chromatography on $SiO_2$ gel, using a gradient elution of hexanes/EtOAc (10:1 to 4:1 to 1:1), afforded 317 mg (2.0 mmol, a 20% yield) of the title compound as a tan solid. MS (ES) m/z: 162 (MH)⁺.

Step 2

8-({2-[3-(2-Naphthyl)-8-azabicyclo[3.2.1]oct-8-yl]ethyl}sulfanyl)quinoline

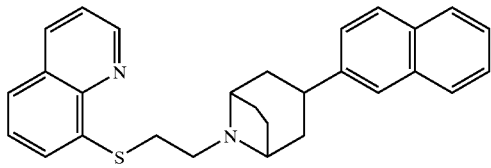

The title compound was prepared by the procedure described in Example 8, Step 5, except that 8-(2-chloroethyl)-3-(2-naphthyl)-8-azabicyclo[3.2.1]octane was used in place of 8-(2-chloroethyl)-3-(2-naphthyl)-8-azabicyclo[3.2.1]oct-2-ene, and 8-quinolinethiol was used in place of 6-methoxyquinolin-8-ol. Yield: 36% of a tan solid. The corresponding oxalate salt was prepared by combining the title compound with 1 equiv. of oxalic acid in $CH_2Cl_2$/MeOH to precipitate a white solid. Yield: 71%; mp: 200–203° C.; MS (ES) m/z: 425.

EXAMPLE 19

The 5-HT transporter affinity of compounds illustrated in Examples 1–18 is established in accordance with standard pharmaceutically accepted test procedures with representative compounds as follows:

Rat Brain ³H-Paroxetine Binding Assay (RB 5HT Transporter):

This assay is used to determine a compound's affinity of the 5-HT transporter.

The protocol is similar to that used by Cheetham et. al. (*Neuropharmacol.* 1993, 32, 737). Briefly, frontal cortical membranes prepared from male S.D. rats are incubated with ³H-parxetine (0.1 nM) for 60 min. at 25° C. All tubes contain either vehicle, test compound (one to eight concentrations), or a saturating concentration of fluoxetine (10 μM) to define specific binding. All reactions are terminated by the addition of ice cold Tris buffer followed by rapid filtration using a Tom Tech filtration device to separate bound from free ³H-paroxetine. Bound radioactivity is quantitated using a Wallac 1205 Beta Plates® counter. Nonlinear regression analysis is used to determine $IC_{50}$ values which are converted to $K_i$ values using the method of Cheng and Prusoff (*Biochem. Pharmacol.* 1973, 22, 3099):

$$K_i = \frac{IC_{50}}{\text{Radioligand concentration}/(1 + KD)}.$$

Inhibition of ³H-5-HT Uptake by Cells Possessing the Human 5-HT Transporter (HC 5HT Transporter):

A human carcinoma cell line (Jar cells) possessing low endogenous levels of the 5-HT-transporter is seeded into 96 well plates and treated with staurosporine at least 18 h prior to assay. [Staurosporine greatly increases the expression of the 5-HT-transporter.] On the day of assay, vehicle, excess of fluoxetine, or test compound is added to various wells on the plate. All wells then receive ³H-5-HT and are incubated at 37° C. for 5 min. The wells are then washed with ice cold 50 mM Tris HCl (pH 7.4) buffer and aspirated to remove free ³H-5-HT. 25 μl of 0.25 M NaOH is then added to each well to lyse the cells and 75 μl scintillation cocktail (Microscint™ 20) added prior to quantitation on a Packard TopCount machine. Tubes with vehicle represent total possible uptake; radioactivity counted in tubes with fluoxetine represent nonspecific binding/uptake and is subtracted from the total possible uptake to give total possible specific uptake. This nonspecific binding (usual low in number) is then subtracted from the counts obtained in wells with various test compounds (or different concentrations of test drug) to give specific uptake in the presence of drug. Specific uptake is then expressed as a % of control values and is analyzed using nonlinear regression analysis (Prizm) to determine $IC_{50}$ values. If the compound is active at inhibiting 5-HT uptake, its counts will be close to that obtained with fluoxetine.

Results from these two assays are presented below in Table I.

TABLE I

Rat Brain $^3$H-Paroxetine Binding Assay (RB 5-HT Transporter) and Inhibition of $^3$H-5-HT Uptake by cells Possessing the Human 5-HT Transporter (HC 5-HT Transporter) Data for Examples 1–18.

| Compound | n | RB 5-HT Transporter $K_i$ (nM) | HC 5-HT Transporter $IC_{50}$ (nM) |
|---|---|---|---|
| Example 1 | 2 | 0.20 | 55.1 |
| Example 2 | 1 | 0.94 | 46.4 |
| Example 3 | 1 | 2.27 | 86.5 |
| Example 4 | 1 | 0.17 | 21.7 |
| Example 5 | 1 | 2.67 | 42.8 |
| Example 6 | 1 | 7.50 | — |
| Example 7 | 1 | 1.61 | — |
| Example 8 | — | — | — |
| Example 9 | 1 | 5.00 | 536 |
| Example 10 | 1 | 1.11 | 58.6 |
| Example 11 | 1 | 34.0 | 191.0 |
| Example 12 | 1 | 0.39 | 35.7 |
| Example 13 | 1 | 0.48 | 42.6 |
| Example 14 | 1 | 0.65 | — |
| Example 15 | 1 | 0.14 | 17.5 |
| Example 16 | 1 | 0.65 | 39.2 |
| Example 17 | 1 | 0.13 | — |
| Examnle 18 | 1 | 0.06 | 3.5 |

The 5-HT$_{1A}$ affinity of the compounds of this invention is established in accordance with standard pharmaceutically accepted test procedures with representative compounds as follows:

Cloning of Human 5-HT$_{1A}$ Receptor:

The PCR cloning of the human 5-HT$_{1A}$ receptor subtype from a human genomic library has been described previously (Chanda et al., 1993). A stable Chinese hamster ovary cell line expressing the human 5-HT$_{1A}$ receptor subtype (h5-HT$_{1A}$.CHO cells) is employed throughout this study. Cells are maintained in DMEM supplemented with 10% fetal calf serum, non-essential amino acids and penicillin/streptomycin.

Radioligand Binding

Cells are grown to 95–100% confluency as a monolayer before membranes are harvested for binding studies. Cells are gently scraped from the culture plates, transferred to centrifuge tubes, and washed twice by centrifugation (2000 rpm for 10 min., 4° C.) in buffer (50 mM Tris; pH 7.5). The resulting pellets are aliquoted and placed at –80 C. On the day of assay, the cells are thawed on ice, and resuspended in buffer. Studies are conducted using [$^3$H]8-OH-DPAT as the radioligand. The binding assay is performed in 96-well microtiter plates in a final total volume of 250 pL of buffer. Competition experiments are performed by using 7 concentrations of unlabelled drug and a final ligand concentration of 1.5 nM. Non-specific binding is determined in the presence of 10 $\mu$M 5HT. Saturation analysis is conducted by using [$^3$H]8-OH-DPAT at concentrations ranging from 0.3–30 nM. Following a 30 minute incubation at room temperature, the reaction is terminated by the addition of ice cold buffer and rapid filtration using a M-96 Brandel Cell Harvester (Gaithersburg, Md.) through a GF/B filter pre-soaked for 30 minutes in 0.5% polyethyleneimine.

$^3$H-Paroxetine Binding to Assess Affinity of Drugs for the Serotonin Transporter (HC 5-HT$_{1A}$ Binding Assay):

A protocol similar to that used by Cheetham et al. (*Neuropharmacol.* 1993, 32, 737) is used to determine the affinity of compounds for the serotonin transporter. Briefly, frontal cortical membranes prepared from male S.D. rats are incubated with $^3$H-paroxetine (0.1 nM) for 60 min at 25° C. All tubes contain either vehicle, test compound (one to eight concentrations), or a saturating concentration of fluoxetine (10 $\mu$M) to define specific binding. All reactions are terminated by the addition of ice cold Tris buffer followed by rapid filtration using a Tom Tech filtration device to separate bound from free $^3$H-paroxetine. Bound radioactivity is quantitated using a Wallac 1205 Beta Plate® counter. Nonlinear regression analysis is used to determine IC$_{50}$ values which are converted to Ki values using the method of Cheng and Prusoff (*Biochem. Pharmacol.* 1973, 22, 3099); Ki=IC$_{50}$/((Radioligand conc.)/(1+KD)).

Assessment of Agonism/Antagonism at the 5-HT$_{1A}$ Receptor using [$^{35}$S]-GTP$\gamma$S Binding to Cloned Human 5-HT$_{1A}$ Receptors:

The [$^{35}$S]-GTP$\gamma$S binding assay is similar to that used by Lazareno and Birdsall (*Br. J. Pharmacol.* 1993, 109, 1120). Briefly, 5-HT$_{1A}$ cloned receptor membrane fragments (as used for 5-HT$_{1A}$ receptor binding assays) are stored at –70° C. until needed. When needed, membranes are rapidly thawed, centrifuged at 40,000× g for 10 minutes and resuspended at 4° C. for 10 minutes in assay buffer (25 mM HEPES, 3 mM MgCl$_2$, 100 mM NaCl, 1 mM EDTA, 10 uM GDP, 500 mM DTT, pH 8.0). These membranes are then incubated for 30 min at 30° C. with [$^{35}$S]GTPgS (1 nM) in the presence of vehicle, test compound (one to eight concentrations), or excess 8-OH-DPAT to define maximum agonist response. All reactions are terminated by the addition of ice cold Tris buffer followed by rapid filtration using a Tom Tech® filtration device to separate bound from free [$^{35}$S]GTPgS. Agonists produce an increase in the amount of [$^{35}$S]GTPgS bound whereas antagonists produce no increase in binding. Bound radioactivity is counted and analyzed as above.

Results from these two assays are presented below in Table II.

TABLE II $^3$H-Paroxetine binding to assess affinity of drugs for the serotonin transporter (HC 5-HT$_{1A}$ affinity) and Assessment of agonism/antagonism at the 5-HT$_{1A}$ receptor using [$^{35}$S]-GTP$\gamma$S binding to cloned human 5-HT$_{1A}$ receptors ([$^{35}$S]GTPgs) Data for Examples 1-X

| Compound | n | HG 5-HT$_{1A}$ affinity $K_i$ (nm) | [$^{35}$S]GTPgS Emax, IC$_{50}$ (nm) |
|---|---|---|---|
| Example 1 | 2 | 295.3 | 25%, 243 nM |
| Example 2 | 2 | 111.1 | 0%, 952 nM |
| Example 3 | 2 | 173.0 | 0% 1169 nM |
| Example 4 | 2 | 329.0 | — |
| Example 18 | 1 | 256.0 | — |

The foregoing data show that the compounds of this invention have substantial affinity for the 5-HT transporter and are useful in the treatment of diseases affected by disorders of the serotonin-affected neurological systems, such as depression and anxiety, by administration orally, parenterally, or by aspiration to a patient in need thereof.

Many variations of the present invention not illustrated herein will occur to those skilled in the art. The present invention is not limited to the embodiments illustrate and described herein, but encompasses all the subject matter within the scope of the appended claims and equivalents thereof.

What is claimed is:

1. A compound of formula I:

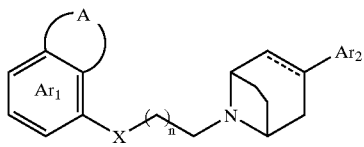

wherein:
A is an optional residue which combines with the carbon atoms to which it is attached to complete a cyclobutyl, cyclohexyl, cycloheptyl, dioxinyl, imidazolyl, pyridinyl, pyridazynyl or pyrimidinyl group;
X is NH, O or S;
n is 0–3;
$Ar_1$ is phenyl or pyridyl substituted with 0–2 $C_1$–$C_3$ alkyl, $C_1$–$C_3$ alkoxy, halo, cyano, nitro, trifluoromethyl, difluoromethyl, hydroxyl, or trifluoromethoxy groups; and,
$Ar_2$ is indolyl, naphthyl, anthracenyl, phenanthrenyl, benzofuryl, or benzothienyl, substituted with 0–2 $C_1$–$C_3$ alkyl, $C_1$–$C_3$ alkoxy, halo, cyano, nitro, trifluoromethyl, difluoromethyl, hydroxyl, or trifluoromethoxy groups,
and all crystalline forms or a pharmaceutically acceptable salt thereof.

2. A compound of formula I according to claim 1 wherein:
A is a residue which combines with the carbon atoms to which it is attached to complete a cyclobutyl, cyclohexyl, cycloheptyl, dioxinyl, imidazolyl, pyridinyl, pyridazynyl or pyrimidinyl group;
X is NH, O or S;
n is 1–2;
$Ar_1$ is a phenyl group substituted with 0–2 $C_1$–$C_3$ alkyl, $C_1$–$C_3$ alkoxy, halo, cyano, trifluoromethyl, hydroxyl, or trifluoromethoxy groups; and,
$Ar_2$ is indolyl, naphthyl, anthracenyl, phenanthrenyl, benzofuryl, or benzothienyl, substituted with 0–2 $C_1$–$C_3$ alkoxy, halo, cyano, nitro, trifluoromethyl, difluoromethyl, hydroxyl, or trifluoromethoxy groups,
and all crystalline forms or a pharmaceutically acceptable salt thereof.

3. A compound according to claim 2 wherein:
A is a residue which combines with the carbon atoms to which it is attached to complete a cyclohexyl or pyridinyl group;
n is 1 or 2;
X is NH or O; and
$Ar_2$ is indolyl, naphthyl, benzofuryl, or benzothienyl, substituted with 0–2 $C_1$–$C_3$ alkoxy, halo, cyano, nitro, trifluoromethyl, difluoromethyl, hydroxyl, or trifluoromethoxy groups;
and all crystalline forms or a pharmaceutically acceptable salt thereof.

4. A compound according to claim 1 selected from the group consisting of:
2-[3-(1H-indol-3-yl)-8-azabicyclo[3.2.1]oct-2-en-8-yl] ethyl 5-quinolinyl ether;
8-[2-(2,3-Dihydro-benzo-[1,4]dioxin-5-yloxy)-ethyl]-3-naphthalen-2-yl-8-aza-bicyclo[3.2.1]oct-2-ene;
6-methoxy-N-{2-[3-(2-naphthyl)-8-azabicyclo[3.2.1]oct-2-en-8-yl]ethyl}-8-quinolinamine;
6-Chloro-N-{2-[3-(2-naphthyl)-8-azabicyclo[3.2.1]oct-2-en-8-yl]ethyl}-8-quinolinamine;
N-{2-[3-(2-naphthyl)-8-azabicyclo[3.2.1]oct-2-en-8-yl]ethyl}-8-quinolinamine;
6-Methoxy-8-[2-(3-naphthalen-2-yl-8-azabicyclo[3.2.1]oct-2-en-8-yl)-ethoxy]quinoline;
3-Naphthalen-2-yl-8-[2-(3-trifluoromethyl-phenoxy)-ethyt]-8-aza-bicyclo[3.2.1]oct-2-ene;
8-{2-[3-(2-Naphthyl)-8-azabicyclo[3.2.1]oct-8-yl]ethoxy}quinoline;
8-({2-[3-(2-naphthyl)-8-azabicyclo[3.2.1]oct-8-yl]ethyl}sulfanyl)quinoline;
and all crystalline forms or pharmaceutically acceptable salts thereof.

5. A composition comprising a pharmaceutically effective amount of a compound according to claim 1 and a pharmaceutically acceptable carrier.

6. A composition comprising a pharmaceutically effective amount of a compound according to claim 2 and a pharmaceutically acceptable carrier.

7. A composition according to claim 5 wherein said compound comprises at least one of
2-[3-(1H-indol-3-yl)-8-azabicyclo[3.2.1]oct-2-en-8-yl] ethyl 5-quinolinyl ether;
8-[2-(2,3-Dihydro-benzo-[1,4]dioxin-5-yloxy)-ethyl]-3-naphthalen-2-yl-8-aza-bicyclo[3.2.1]oct-2-ene;
6-methoxy-N-{2-[3-(2-naphthyl)-8-azabicyclo[3.2.1]oct-2-en-8-yl]ethyl}-8-quinolinamine;
6-Chloro-N-{2-[3-(2-naphthyl)-8-azabicyclo[3.2.1]oct-2-en-8-yl]ethyl}-8-quinolinamine;
N-{2-[3-(2-naphthyl)-8-azabicyclo[3.2.1]oct-2-en-8-yl]ethyl}-8-quinolinamine;
6-Methoxy-8-[2-(3-naphthalen-2-yl-8-azabicyclo[3.2.1]oct-2-en-8-yl)-ethoxy]-quinoline;
3-Naphthalen-2-yl-8-[2-(3-trifluoromethyl-phenoxy)-ethyl]-8-aza-bicyclo[3.2.1]oct-2-ene;
8-{2-[3-(2-Naphthyl)-8-azabicyclo[3.2.1]oct-8-yl]ethoxy}quinoline;
8-({2-[3-(2-naphthyl)-8-azabicyclo[3.2.1]oct-8-yl]ethyl}sulfanyl)quinoline;
or all crystalline forms or pharmaceutically acceptable salts thereof.

8. A process for making a compound of formula I, as set forth in claim 2, wherein X=NH, $Ar_1$ is phenyl and A combines with the carbon atoms to which it is attached to complete a 2-pyridinyl group, said process comprising reacting the corresponding 8-haloquinoline with the corresponding $Ar_2$-8-azabicyclo[3.2.1]-octane/octene-$CH_2$—$(CH_2)_n$ $NH_2$ compound in the presence of NaOt-Bu and a suitable catalyst.

9. A process for making a compound of formula I, as set forth in claim 2, wherein X=O or S, $Ar_1$ is phenyl and A combines with the carbon atoms to which it is attached to complete a 2-pyridinyl group, said process comprising reacting the corresponding 8-XH-quinoline compound with the corresponding $Ar_2$-8-azabicyclo[3.2.1]-octane/octene-$CH_2$—$(CH_2)_n$-halide compound in the presence of NaH.

10. A method for treating depression comprising administering to a patient in need thereof an effective amount of a compound according to claim 1.

11. A compound of formula I:

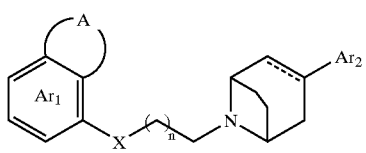

wherein:
A is an optional residue which combines with the carbon atoms to which it is attached to complete a cyclobutyl, cyclopentyl, cyclohexyl, cycloheptyl, dioxinyl, pyrrolyl, imidazolyl, pyridinyl, pyridazynyl or pyrimidinyl group;
X is NH or S;
n is 0–3;
$Ar_1$ is phenyl or pyridyl substituted with 0–2 $C_1$–$C_3$ alkyl, $C_1$–$C_3$ alkoxy, halo, cyano, nitro, trifluoromethyl, difluoromethyl, hydroxyl, or trifluoromethoxy groups; and,
$Ar_2$ is indolyl, benzimidazolyl, naphthyl, anthracenyl, phenanthrenyl, benzofuryl, or benzothienyl, substituted with 0–2 $C_1$–$C_3$ alkyl, $C_1$–$C_3$ alkoxy, halo, cyano, nitro, trifluoromethyl, difluoromethyl, hydroxyl, or trifluoromethoxy groups,
and all crystalline forms or a pharmaceutically acceptable salt thereof.

12. A process for making a compound of formula I, as set forth in claim 11, wherein X represents NH or S, and A combines with the carbon atoms to which it is attached to complete a 2-pyrrolyl group, which process comprises reacting the corresponding $Ar_2$-8-azabicyclo[3.2.1]-octane or -octene compound with the corresponding pyrrolyl-$Ar_1$—X—$(CH_2)_n$—$CH_2$-halide in the presence of a base.

13. A compound of formula:

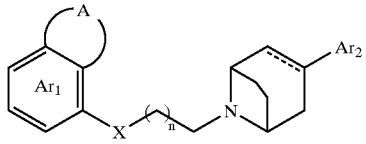

wherein:
A is a residue which combines with the carbon atoms to which it is attached to complete a cyclobutyl, cyclopentyl, cyclohexyl, cycloheptyl, dioxinyl, pyrrolyl, imidazolyl, pyridinyl, pyridazynyl or pyrimidinyl group;
X is O;
n is 0–3;
$Ar_1$ is phenyl or pyridyl substituted with 0–2 $C_1$–$C_3$ alkyl, $C_1$–$C_3$ alkoxy, halo, cyano, nitro, trifluoromethyl, difluoromethyl, hydroxyl, or trifluoromethoxy groups; and,
$Ar_2$ is phenyl substituted with 0–2 $C_1$–$C_3$ alkyl, $C_1$–$C_3$ alkoxy, halo, cyano, nitro, trifluoromethyl, difluoromethyl, hydroxyl, or trifluoromethoxy groups,
and all crystalline forms or a pharmaceutically acceptable salt thereof.

14. A compound according to claim 13 wherein A is a residue which combines with the carbon atoms to which it is attached to complete a pyrrolyl group and $Ar_1$ is phenyl substituted with 0–2 $C_1$–$C_3$ alkyl, $C_1$–$C_3$ alkoxy, halo, cyano, nitro, trifluoromethyl, difluoromethyl, hydroxyl, or trifluoromethoxy groups.

15. A compound according to claim 13 selected from the group consisting of:
4-{2-[3-(3,4-Dichloro-phenyl)-8-azabicyclo[3.2.1]oct-2-en-8-yl]-ethoxy}-1H-indole;
4-{3-[3-(3,4-Dichlorophenyl)-8-azabicyclo[3.2.1]oct-2-en-8-yl]propoxy-1H-indole; and
all crystalline forms or pharmaceutically acceptable salts thereof.

16. A compound of formula I:

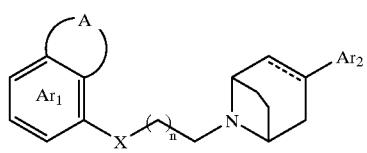

wherein:
A is a residue which combines with the carbon atoms to which it is attached to complete a cyclopentyl or pyrrolyl group;
X is O;
n is 1 to 2;
$Ar_1$ is phenyl substituted with 0–2 $C_1$–$C_3$ alkyl, $C_1$–$C_3$ alkoxy, halo, cyano, nitro, trifluoromethyl, difluoromethyl, hydroxyl, or trifluoromethoxy groups; and,
$Ar_2$ is naphthyl substituted with 0–2 $C_1$–$C_3$ alkyl, $C_1$–$C_3$ alkoxy, halo, cyano, nitro, trifluoromethyl, difluoromethyl, hydroxyl, or trifluoromethoxy groups;
and all crystalline forms or a pharmaceutically acceptable salt thereof.

17. A compound of claim 16 wherein $Ar_2$ is napthyl substituted with 0–2 $C_1$–$C_3$ alkyl, $C_1$–$C_3$ alkoxy, cyano, nitro, or trifluoromethyl groups;
and all crystalline forms or a pharmaceutically acceptable salt thereof.

18. A compound selected from the group consisting of:
4-[2-(3-Naphthalen-2-yl-8-aza-bicyclo[3.2.1]oct-2-en-8-yl)-ethoxy]-1-H-indole;
8-[2-(Indan-4-yloxy)-ethyl]-3-naphthalen-2-yl-8-azabicyclo[3.2.1]oct-2-ene;
4-{2-[3-(6-Methoxy-naphthalen-2-yl)-8-aza-bicyclo[3.2.1]oct-2-en-8-yl]-ethoxy}-1H-indole;
4-[2-(3-Naphthalen-2-yl-8-aza-bicyclo[3.2.1]oct-8-yl)-ethoxy]-1H-indole;
4-[3-(3-Naphthalen-2-yl-8-aza-bicyclo[3.2.1]oct-2-en-8-yl)-propoxy]-1H-indole;
and all crystalline forms or pharmaceutically acceptable salts thereof.

19. A compound of formula I:

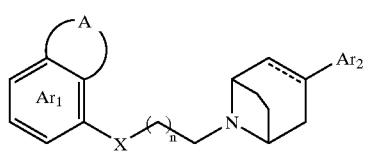

wherein:
A is a residue which combines with the carbon atoms to which it is attached to complete a pyrrolyl group;

X is O;

n is 1 to 2;

Ar$_1$ is phenyl substituted with 0–2 C$_1$–C$_3$ alkyl, C$_1$–C$_3$ alkoxy, halo, cyano, nitro, trifluoromethyl, difluoromethyl, hydroxyl, or trifluoromethoxy groups; and, Ar$_2$ is indolyl substituted with 0–2 C$_1$–C$_3$ alkyl, C$_1$–C$_3$ alkoxy, halo, cyano, nitro, trifluoromethyl, difluoromethyl, hydroxyl, or trifluoromethoxy groups;

and all crystalline forms or a pharmaceutically acceptable salt thereof.

20. A compound of claim 19 wherein n is 1, and the double bond is present.

21. A compound of claim 20 wherein Ar$_2$ is indolyl substituted with 0–2 C$_1$–C$_3$ alkyl, C$_1$–C$_3$ alkoxy, cyano, nitro, or trifluoromethyl groups.

22. A compound of claim 19 which is:

3-{8-[2-(1H-Indol-4-yloxy)ethyl]-8-azabicyclo[3.2.1]oct-2-en-3-yl}-1H-indole;

and all crystalline forms or pharmaceutically acceptable salts thereof.

* * * * *